(12) United States Patent
Schock et al.

(10) Patent No.: US 7,377,935 B2
(45) Date of Patent: May 27, 2008

(54) APPARATUS FOR ALTERING THE BODY TEMPERATURE OF A PATIENT

(75) Inventors: Robert B. Schock, Sparta, NJ (US); Marc Cote, Cornwall, NY (US)

(73) Assignee: Life Recovery Systems HD, LLC, Alexandria, LA (US)

( * ) Notice: Subject to any disclaimer, the term of this patent is extended or adjusted under 35 U.S.C. 154(b) by 470 days.

(21) Appl. No.: 10/948,918

(22) Filed: Sep. 24, 2004

(65) Prior Publication Data
US 2006/0069418 A1    Mar. 30, 2006

(51) Int. Cl.
*A61F 7/00* (2006.01)

(52) U.S. Cl. ...................... 607/104; 607/108

(58) Field of Classification Search ......... 607/104–112
See application file for complete search history.

(56) References Cited

U.S. PATENT DOCUMENTS

| | | | |
|---|---|---|---|
| 26,663 | A | 1/1860 | French |
| 998,804 | A | 7/1911 | Salisbury |
| 1,936,960 | A | 11/1933 | Bowman |
| 2,093,834 | A | 9/1937 | Gaugler |
| 2,272,481 | A | 2/1942 | Rinkes et al. |
| 2,493,067 | A | 1/1950 | Goldsmith |
| 2,566,600 | A | 9/1951 | Colon |
| 2,702,552 | A | 2/1955 | Moodie |
| 2,832,336 | A | 4/1958 | Davis et al. |
| 3,051,180 | A | 8/1962 | Adams-Ray et al. |
| 3,266,064 | A | 8/1966 | Figman |
| 3,477,424 | A | 11/1969 | Tracy |
| 3,587,577 | A | 6/1971 | Smirnov et al. |
| 3,757,362 | A | 9/1973 | Bowlin et al. |
| 3,866,994 | A | 2/1975 | Bonin |
| 4,057,861 | A | 11/1977 | Howorth |
| 4,074,369 | A | 2/1978 | Harmon |
| 4,139,004 | A | 2/1979 | Gonzalez |
| 4,141,585 | A | 2/1979 | Blackman |
| 4,149,529 | A | 4/1979 | Copeland et al. |

(Continued)

FOREIGN PATENT DOCUMENTS

GB    WO 1095988    12/1967

(Continued)

OTHER PUBLICATIONS

International Search Report dated Jan. 31, 2006, 3 pages.

(Continued)

*Primary Examiner*—Roy D. Gibson
(74) *Attorney, Agent, or Firm*—Armstrong Teasdale, LLP

(57) ABSTRACT

Apparatus for altering the body temperature of a patient comprises a cover for covering at least a portion of a patient's body and a compliant support adapted to underlie and generally conform to the shape of the portion of the patient's body to define a well adjacent to the patient's body portion for accumulating heat transfer liquid. The cover and compliant support cooperatively define an enclosure for receiving the portion of the patient's body and are constructed to conduct a heat transfer liquid into direct contact with the portion of the patient's body received in the enclosure to promote heat transfer between the patient's body and the heat transfer liquid.

42 Claims, 16 Drawing Sheets

U.S. PATENT DOCUMENTS

| | | |
|---|---|---|
| 4,191,028 A | 3/1980 | Audet et al. |
| 4,353,359 A | 10/1982 | Milbauer |
| 4,376,437 A | 3/1983 | Sundheim et al. |
| 4,572,188 A | 2/1986 | Augustine et al. |
| 4,648,392 A | 3/1987 | Cartier et al. |
| 4,691,762 A | 9/1987 | Elkins et al. |
| 4,738,119 A | 4/1988 | Zafred |
| 4,747,408 A | 5/1988 | Chuan-Chih |
| 4,765,338 A | 8/1988 | Turner et al. |
| D300,194 S | 3/1989 | Walker |
| 4,858,259 A | 8/1989 | Simmons et al. |
| 4,945,901 A | 8/1990 | Burcke, Jr. |
| 4,959,877 A | 10/1990 | Covil |
| 4,962,761 A | 10/1990 | Golden |
| 4,987,618 A | 1/1991 | Tolbert |
| 4,987,896 A | 1/1991 | Nakamatsu |
| 5,016,304 A | 5/1991 | Ryhiner |
| 5,033,136 A | 7/1991 | Elkins |
| 5,074,285 A | 12/1991 | Wright |
| 5,146,625 A | 9/1992 | Steele et al. |
| 5,149,331 A | 9/1992 | Ferdman et al. |
| 5,172,689 A | 12/1992 | Wright |
| 5,235,709 A | 8/1993 | Terlep |
| 5,241,958 A | 9/1993 | Noeldner |
| 5,243,706 A | 9/1993 | Frim et al. |
| 5,246,061 A | 9/1993 | Zalite |
| 5,249,318 A | 10/1993 | Loadsman |
| 5,265,599 A | 11/1993 | Stephenson et al. |
| 5,292,347 A | 3/1994 | Pompei |
| 5,300,100 A | 4/1994 | Hickle et al. |
| 5,305,471 A | 4/1994 | Steele et al. |
| D347,491 S | 5/1994 | Holloway |
| 5,336,250 A | 8/1994 | Augustine |
| 5,342,411 A | 8/1994 | Maxted et al. |
| 5,350,417 A | 9/1994 | Augustine |
| 5,358,467 A | 10/1994 | Milstein et al. |
| 5,383,918 A | 1/1995 | Panetta |
| 5,405,370 A | 4/1995 | Irani |
| 5,411,494 A | 5/1995 | Rodriguez |
| 5,416,935 A | 5/1995 | Nieh |
| D360,692 S | 7/1995 | Gambino |
| 5,441,477 A | 8/1995 | Hargest |
| 5,447,504 A | 9/1995 | Baker |
| D365,378 S | 12/1995 | Wolfe |
| D366,084 S | 1/1996 | Wolfe |
| 5,507,792 A | 4/1996 | Mason et al. |
| 5,584,084 A | 12/1996 | Klearman et al. |
| 5,603,728 A | 2/1997 | Pachys |
| 5,642,539 A | 7/1997 | Kuo |
| D383,834 S | 9/1997 | Frankel |
| 5,683,438 A | 11/1997 | Grahn |
| 5,688,225 A | 11/1997 | Walker |
| 5,722,482 A | 3/1998 | Buckley |
| 5,755,756 A | 5/1998 | Freedman, Jr. et al. |
| 5,800,480 A | 9/1998 | Augustine et al. |
| 5,817,147 A | 10/1998 | Wolf |
| D405,291 S | 2/1999 | Yu |
| 5,871,526 A | 2/1999 | Gibbs et al. |
| 5,887,304 A | 3/1999 | von der Heyde |
| D410,084 S | 5/1999 | Tumey |
| 5,913,885 A | 6/1999 | Klatz et al. |
| 5,913,886 A | 6/1999 | Soloman |
| 5,927,273 A | 7/1999 | Federowicz et al. |
| 5,950,234 A | 9/1999 | Leong et al. |
| 5,957,964 A | 9/1999 | Ceravolo |
| 5,975,081 A | 11/1999 | Hood et al. |
| 5,989,285 A * | 11/1999 | DeVilbiss et al. .......... 607/107 |
| 5,991,948 A | 11/1999 | Stanley et al. |
| 6,030,412 A | 2/2000 | Klatz et al. |
| 6,052,853 A | 4/2000 | Schmid |
| 6,109,338 A | 8/2000 | Butzer |
| 6,128,795 A * | 10/2000 | Stanley et al. .................. 5/421 |
| D433,508 S | 11/2000 | Crowther |
| 6,149,674 A | 11/2000 | Borders |
| 6,165,208 A | 12/2000 | Reyes et al. |
| D436,175 S | 1/2001 | Tumey |
| 6,182,316 B1 | 2/2001 | Thomas et al. |
| 6,183,855 B1 | 2/2001 | Buckley |
| D438,623 S | 3/2001 | Tantau |
| 6,197,045 B1 | 3/2001 | Carson |
| 6,210,427 B1 | 4/2001 | Augustine et al. |
| 6,228,106 B1 | 5/2001 | Simbruner et al. |
| 6,245,094 B1 | 6/2001 | Pompei |
| 6,276,155 B2 | 8/2001 | Siman-Tov et al. |
| 6,277,144 B1 | 8/2001 | Tomic-Edgar et al. |
| 6,375,674 B1 | 4/2002 | Carson |
| D461,900 S | 8/2002 | Siepmann |
| 6,461,379 B1 | 10/2002 | Carson et al. |
| 6,508,831 B1 | 1/2003 | Kushnir |
| 6,517,510 B1 | 2/2003 | Stewart et al. |
| 6,520,982 B1 | 2/2003 | Boynton et al. |
| D474,061 S | 5/2003 | Cook |
| 6,565,593 B2 | 5/2003 | Diana |
| 6,602,277 B2 | 8/2003 | Grahn et al. |
| 6,620,187 B2 | 9/2003 | Carson et al. |
| 6,645,232 B2 | 11/2003 | Carson |
| 6,656,208 B2 | 12/2003 | Grahn et al. |
| 6,660,027 B2 | 12/2003 | Gruszecki et al. |
| 6,673,098 B1 | 1/2004 | Machold |
| 6,673,099 B2 | 1/2004 | Grahn et al. |
| 6,682,550 B2 | 1/2004 | Clifton et al. |
| 6,685,731 B2 | 2/2004 | Kushnir et al. |
| 6,692,518 B2 | 2/2004 | Carson |
| 6,695,872 B2 | 2/2004 | Elkins |
| 6,699,267 B2 | 3/2004 | Voorhees et al. |
| 6,709,447 B1 | 3/2004 | Gammons |
| 6,718,785 B2 | 4/2004 | Bieberich |
| 6,730,115 B1 | 5/2004 | Heaton |
| 6,743,250 B2 | 6/2004 | Renfro |
| 6,749,624 B2 | 6/2004 | Knowlton |
| 6,764,502 B2 | 7/2004 | Bieberich |
| 6,799,063 B2 | 9/2004 | Carson |
| 6,800,087 B2 | 10/2004 | Papay et al. |
| 6,800,088 B1 | 10/2004 | Karapetyan |
| 6,802,855 B2 | 10/2004 | Ellingboe et al. |
| 6,818,012 B2 | 11/2004 | Ellingboe |
| D527,822 S | 9/2006 | Trevino |
| 2003/0024684 A1 | 2/2003 | Lyons et al. |
| 2003/0097163 A1 | 5/2003 | Kane et al. |
| 2003/0125649 A1 | 7/2003 | McIntosh et al. |
| 2003/0195596 A1 | 10/2003 | Augustine et al. |
| 2003/0236561 A1 | 12/2003 | Lennox |
| 2004/0049252 A1 | 3/2004 | Gluderer |
| 2004/0064170 A1 | 4/2004 | Radons et al. |
| 2004/0064171 A1 | 4/2004 | Briscoe et al. |
| 2004/0093050 A1 | 5/2004 | Beard et al. |
| 2004/0158303 A1 | 8/2004 | Lennox et al. |
| 2004/0186537 A1 | 9/2004 | Heaton et al. |
| 2004/0187512 A9 | 9/2004 | Becker et al. |
| 2004/0204748 A1 | 10/2004 | Hansen et al. |
| 2004/0225341 A1 | 11/2004 | Schock et al. |
| 2004/0243202 A1 | 12/2004 | Lennox |
| 2005/0060012 A1 | 3/2005 | Voorhees et al. |

FOREIGN PATENT DOCUMENTS

| | | |
|---|---|---|
| WO | WO 98/40039 A1 | 9/1988 |
| WO | WO 88/10074 A1 | 12/1988 |
| WO | WO 94/05238 A1 | 3/1994 |
| WO | WO 96/13234 A1 | 5/1996 |
| WO | WO 99/09916 A1 | 3/1999 |
| WO | WO 99/39678 A1 | 8/1999 |
| WO | WO 99/44552 A1 | 9/1999 |

WO        WO 01/50988 A1    7/2001

OTHER PUBLICATIONS

Bernard, S.A., et al., "Treatment of Comatose Survivors of Out-of-Hospital Cardiac Arrest with Induced Hypothermia", New England Journal of Medicine, Feb. 21, 2002, pp. 557-563, vol. 346, No. 8, Massachusetts Medical Society, Boston, Massachusetts, United States.

Blair, D., et al., "The Increase in Tone in Forearm Resistance Blood Vessels Exposed to Increased Transmural Pressure", The Journal of Physiology, Jul. 1959, pp. 614-625, vol. 149, Cambridge University Press, London, Great Britain.

Felberg, R., et al., "Hypothermia After Cardiac Arrest: Feasibility and Safety of an External Cooling Protocol", Circulation, 2001, pp. 1799-1804, vol. 104, American Heart Association, Dallas, Texas, United States.

Future Medical Products, Inc., "Enhanced External Counterpulsation (EECP) Fact Sheet", Mar. 1994, pp. 1-3.

Grahn, D., et al., "Recovery from Mild Hypothermia can be Accelerated by Mechanically Distending Blood Vessels in the Hand", Journal of Applied Physiology, Nov. 1998, pp. 1643-1648, vol. 85, No. 5, The American Physiological Society, Bethesda, Maryland, United States.

Henriksen, O., "Local Sympathetic Reflex Mechanism in Regulation of Blood Flow in Human Subcutaneous Adipose tissue", ACTA Physiologica Scandinavica, 1977, 48 pages, Supplement 450, Almqvist & Wiksell, Uppsala, Sweden.

Henriksen, O., "Sympathetic Reflex Control of Blood Flow in Human Peripheral Tissues", ACTA Physiologica Scandinavica, 1991, pp. 33-39, vol. 143, Supplement 603, ACTA Physiologica Scandinavica, Stockholm, Sweden.

Holzer, M., et al., "Mild Therapeutic Hypothermia to Improve the Neurologic Outcome after Cardiac Arrest", New England Journal of Medicine, Feb. 21, 2002, pp. 549-556, vol. 346, No. 8, Massachusetts Medical Society, Boston, Massachusetts, United States.

Oakley, E., et al., "Can Recovery From Mild Hypothermia be Accelerated so Much by Mechanically Distending Locally Heated Blood Vessels?", Journal of Applied Physiology, Aug. 1999, pp. 867-868, vol. 87, No. 2, The American Physiology Society, Bethesda, Maryland, United States.

Janicki, et al., "Comparison of Two Different Temperature Maintenance Strategies During Open Abdominal Surgery", Anesthesiology, Oct. 2001, pp. 868-874, vol. 95.

Kirklin, et al., "Hypothermia, Circulatory Arrest, and Cardiopulmonary Bypass", Chapter 2, 1993, pp. 113-114, vol. 1, Second Edition, Churchill Livingston.

Koscheyev et al., "Augmentation of Blood Circulation to the Fingers by Warming Distant Body Areas", European Journal of Applied Physiology and Occupational Physiology (2000), pp. 103-111, 82.

Lawson, W.E., et al., "Efficacy of Enhanced External Counterpulsation in the Treatment of Angina Pectoris", 1992, p. 1.

Mellergard, "Changes in Human Intracerebral Temperature in Response to Different Methods of Brain Cooling", Neurosurgery, Oct. 1992, pp. 671-677, vol. 31, No. 4.

Nag, et al., "Efficacy of a Water-Cooled Garment for Auxiliary Body Cooling in Heat", Ergonomics, 1998, pp. 179-187, vol. 41, No. 2.

Nesher, et al., "A Novel Thermoregulatory System Maintains Peroperative Normothermia in Children Undergoing Elective Surgery", Pediatric Anesthesia, 2001, pp. 555-560.

Oster, M.D., "Guidelines for the Submission of Abstracts", Apr. 30, 1993, p. 1.

Plattner, et al., "Efficacy of Intraoperative Cooling Methods", Anesthesiology, Nov. 1997, pp. 1089-1095, vol. 87(5), printed from www.anesthesiology.org.

Raven, et al., "Hemodynamic Changes During Whole Body Surface Cooling and Lower Body Negative Pressure", Aviation, Space, and Environmental Medicine, Jul. 1981, pp. 387-391.

Taguchi, A., et al., "Negative Pressure Rewarming vs. Forced Air Warming in Hypothermic Postanesthetic Volunteers", Anesthesia & Analgesia, Jan. 2001, pp. 261-266, vol. 92, No. 1, International Anesthesia Research Society et al., San Francisco, California, United States.

Wolthuis, R., et al., "Physiological Effects of Locally Applied Reduced Pressure in Man", Physiological Reviews, 1974, pp. 566-595, vol. 54, The American Physiological Society, Bethesda, Maryland, United States.

"Treatment of Refractory Fever in Neurosciences Critical Care Unit Using a Novel, Water-Circulating Cooling Device", Journal of Neurosurgical Anesthesiology, vol. 15, No. 4, pp. 313-318, 2003.

Effects of Inducted Hypothermia on Samatosensory Evoked Potentials in Patients with Chronic Spinal Cord Injury, Paraplegia 31, 730-741, 1993.

Gardella et al., "Lowering Body Temperature with a Cooling Suit as Symptomatic Treatment for Thermosensitive Multiple Scherosis Patients", Ital. J. Neurol. Sci., 1995.

Syndulko et al., "Preliminary Evaluation of Lowering Tympani Temperature for the Symptomatic Treatment of Multiple Sclerosis", J. Neuro. Rehab., vol. 9, No. 4, 1995.

Ku et al., "Hemodynamic and Thermal Responses to Head and Neck Cooling in Men and Women", Am J Phys Med Rehabil, 75:443-450, 1996.

Spinoff, "New Help for MS Patients" 1993.

"Acute Effects of Cooling in Multiple Sclerosis: Pilot Study to Compare Two Cooling Garments", 1995.

Flenser et al., "The Cooling-Suit: Case Studies of its Influence on Fatigue Amoung Eight Individuals with Multiple Sclerosis", Journal of Advanced Nursing 37(6), 541-550, Mar. 2002.

Ku et al., "Physiologic and Functional Responses of MS Patients to Body Cooling", Multiple Sclerosis, Sep./Oct. 2000, 427-434.

Regan et al., "Effect of body temperature on visual evoked potential delay and visual perception in multiple sclerosis", Journal of Neurology, Neurosurgery, and Psychiatry, 1977, 40, 1083-1091.

Greenleaf, et al., Fluid-electrolyte shifts and thermoregulation: Rest and work in heat with head cooling, Aug. 1980, vol. 51, No. 8, ASEMCG 5(8): 747-850.

* cited by examiner

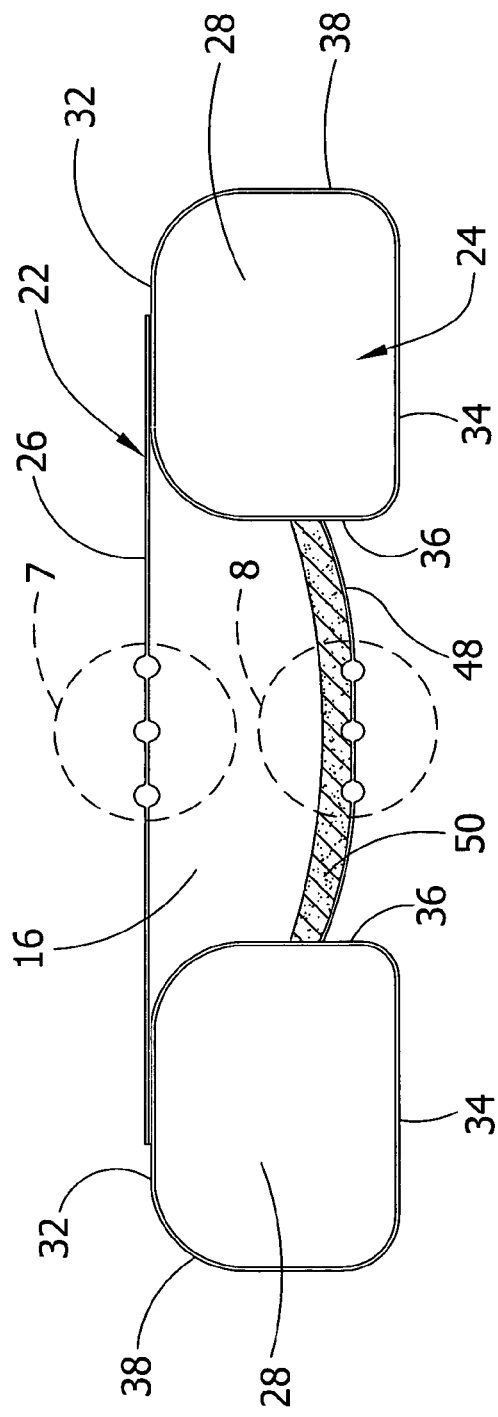
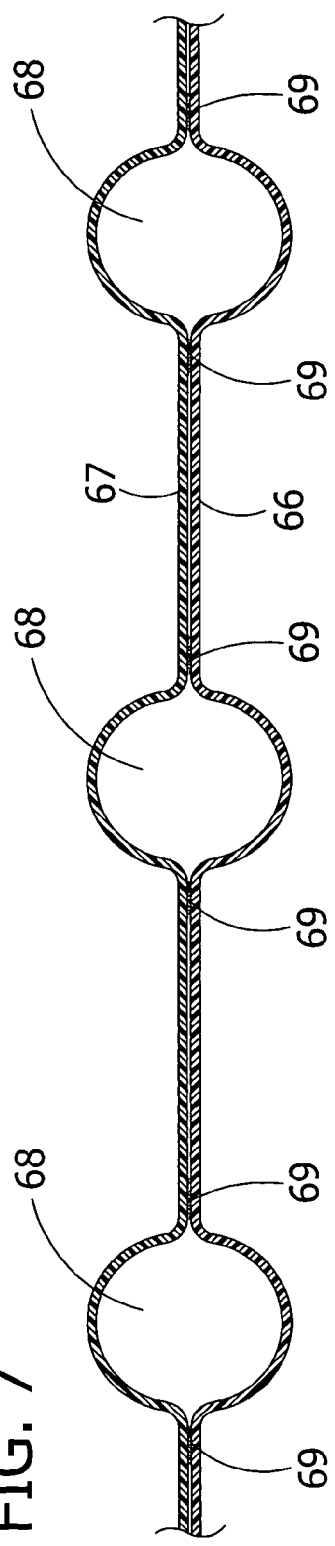
FIG. 6
FIG. 7

APPARATUS FOR ALTERING THE BODY TEMPERATURE OF A PATIENT

BACKGROUND OF THE INVENTION

This invention generally relates to medical apparatus for altering the body temperature of a patient and more particularly to apparatus that enables efficient, quick adjustment of the body temperature of a patient, especially to induce hypothermia.

Sudden cardiac arrest remains a serious public health issue. Approximately 350,000 individuals are stricken in the United States annually, with overall survival rates of roughly 5 percent. Even with the immediate availability of the most advanced care currently available, including cardiopulmonary resuscitation (CPR), drugs, ventilation equipment, and automatic external defibrillators, a survival rate of 25 percent may be the probable best case scenario. Improved therapies to deal with this condition are clearly needed.

Numerous incidences of recovery following accidental hypothermia and cardiac arrest have been reported. This observation has led researchers to consider therapeutic hypothermia as a possible treatment for reducing the adverse consequences of circulatory arrest. Various studies have shown that moderate systemic hypothermia (approximately 3-5° C. (5.4-9.0° F.)) can reduce damage to vital organs, including the brain. Hypothermia induced both during and following cardiac arrest has demonstrated this benefit. The use of cardiopulmonary bypass has also been effective in rapidly achieving this goal. Direct flushing of cooled fluids into the arterial system has also been employed with success. Both invasive measures, however, require large bore intravascular catheters and rapid introduction of sterile solutions into the patient. Such invasive approaches have obvious disadvantages in dealing with out-of-hospital emergencies.

Noninvasive cooling, if sufficiently effective and portable, would be a preferable approach. Direct cooling of the head alone has produced variable results. However, post-resuscitative cooling of the entire body to approximately 33° C. (91.4° F.) by noninvasive treatment has been demonstrated to be surprisingly effective in recent clinical studies. The use of cold gel and ice packs produced cooling of approximately 0.9° C. (1.6° F.) per hour, and resulted in a nearly 100 percent improvement in neurologically intact survival (Bernard S. A. et al., *Treatment of Comatose Survivors of Out-of-Hospital Cardiac Arrest with Induced Hypothermia*, 346 NEW ENG. J. MED. 557-563 (2002)). In another study, cold air was found to be capable of cooling patients at a rate of about 0.25° C. (0.45° F.) per hour, which caused a 40 percent improvement in the same endpoint (Sterz F. et al., *Mild Therapeutic Hypothermia to Improve the Neurologic Outcome after Cardiac Arrest*, 346 NEW ENG. J. MED. 549-556 (2002)). In yet another study, a combination of water-filled cooling blankets and ice packs applied to the skin resulted in a cooling rate of 0.8° C. (1.4° F.) per hour (Felberg et al., *Hypothermia After Cardiac Arrest—Feasibility and Safety of an External Cooling Protocol*, 104 CIRCULATION 1799-1804 (2001)). It is believed that increasing the rate of cooling from what is shown in these studies may produce a higher rate of patient salvage.

SUMMARY OF THE INVENTION

The present invention is directed to apparatus for altering the body temperature of a patient. The apparatus generally comprises a cover for covering at least a portion of a patient's body, and a compliant support. The cover and compliant support cooperatively define an enclosure for receiving the portion of the patient's body and are constructed to conduct a heat transfer liquid into direct contact with the portion of the patient's body received in the enclosure to promote heat transfer between the patient's body and the heat transfer liquid. The compliant support is adapted to underlie and generally conform to the shape of the portion of the patient's body to define a well adjacent to the patient's body portion for accumulating heat transfer liquid.

In another aspect, the apparatus generally comprises an enclosure adapted for receiving at least the torso and the legs of a patient. The enclosure is capable of conforming to the shape and size of the patient's body to thereby accommodate patients of various shapes and sizes. A liquid delivery system is capable of driving heat transfer liquid into the enclosure for direct contact with at least a portion of the patient's torso received in the enclosure to promote heat transfer between the patient's body and the heat transfer liquid.

In yet another aspect, the apparatus generally comprises an enclosure defining an interior space for receiving at least a portion of a patient's body therein and constructed for directing heat transfer fluid into direct contact with the portion of the patient's body received in the interior space. The enclosure is formed at least in part of a flexible material. A fluid passage in the enclosure is constructed and arranged for directing heat transfer liquid into the enclosure. At least a portion of the fluid passage is defined by the flexible material. A hold-open is received in the portion of the fluid passage defined by the flexible material to hold the passage open and permit flow of a heat transfer liquid through the fluid passage past the hold-open.

In yet another aspect, the apparatus generally comprises an enclosure defining an interior space for receiving a portion of a patient's body. At least one inlet is disposed above the portion of the patient's body for directing heat transfer liquid into the interior space to flow over the patient's body portion, and at least one inlet is disposed below the portion of the patient's body when received in the interior space for directing heat transfer liquid into the interior space to flow under the patient's body portion.

In still another aspect, the apparatus generally comprises an enclosure defining an interior space for receiving at least a portion of a patient's body therein. An inlet in the enclosure allows a heat transfer liquid to flow into the enclosure for direct contact with the portion of the patient's body received in the enclosure to promote heat transfer between the patient's body and the heat transfer liquid. An outlet in the enclosure allows the heat transfer liquid to be exhausted from the enclosure. A flow restrictor is in fluid communication with the outlet for maintaining a predetermined amount of heat transfer liquid in the enclosure.

In a further aspect, a system is operable in a liquid cooling mode and a gas cooling mode for adjusting the body temperature of a patient. The system generally comprises an enclosure defining an interior space for receiving at least a portion of a patient's body therein. A liquid delivery system controls the temperature of liquid and drives the liquid into the enclosure in the liquid cooling mode into direct contact with the patient's body portion when received in the enclosure. A gas delivery system controls the temperature of gas and drives the gas into the enclosure in the gas cooling mode into direct contact with the patient's body portion when received in the enclosure.

In still a further aspect, the apparatus generally comprises an enclosure defining an interior space for receiving at least a portion of a patient's body therein. The enclosure is generally contiguous with the portion of the patient's body received in the interior space of the enclosure. The enclosure is also adapted to admit a heat transfer fluid into direct contact with the portion of the patient's body received in the enclosure to promote heat transfer between the patient's body and the heat transfer fluid. A filtration system filters the heat transfer fluid.

In another aspect, the apparatus generally comprises an enclosure defining an interior space for receiving at least a portion of a patient's body therein. The enclosure is adapted to admit a heat transfer fluid into direct contact with the portion of the patient's body received in the interior space to promote heat transfer between the patient's body and the heat transfer fluid. The enclosure includes indicia arranged for positioning a portion of the patient's body relative to the enclosure.

In yet another aspect, the apparatus generally comprises an enclosure adapted for receiving at least the portion of a patient's body. A pump is capable of driving heat transfer fluid into the enclosure for direct contact with at least a portion of the patient's body received in the enclosure to promote heat transfer between the patient's body and the heat transfer fluid. At least one valve can selectively adjust the flow path of the heat transfer fluid such that the heat transfer fluid can be directed to selected portions of the enclosure.

In a further aspect, the apparatus generally comprises an enclosure having an interior space adapted for receiving at least a portion of a patient's body. A liquid delivery system is capable of driving heat transfer liquid into the interior space of the enclosure for direct contact with at least a portion of the patient's body received in the enclosure to promote heat transfer between the patient's body and the heat transfer liquid. A plurality of inlets are in fluid communication with the interior space of the enclosure for allowing the heat transfer liquid driven by the liquid delivery system to pass through the inlet and into the interior space of the enclosure. The inlets are positioned for directing the heat transfer liquid to preselected parts of the portion of the patient's body received in the interior space of the enclosure such that a greater volume of heat transfer liquid flows over the preselected parts of the portion of the patient's body than non-selected parts of the portion of the patient's body.

In still a further aspect, the apparatus generally comprises an enclosure defining an interior space for receiving at least a portion of a patient's body therein. The enclosure is adapted to admit a heat transfer fluid into direct contact with the portion of the patient's body received in the enclosure to promote heat transfer between the patient's body and the heat transfer fluid. A head rest is adapted to position the patient's head at an angle suitable for mouth-to-mouth resuscitation.

In yet a further aspect, the apparatus generally comprises a compliant support that is sized and shaped for receiving a portion of the patient's body and constructed to conduct a heat transfer liquid into direct contact with the portion of the patient's body received in the enclosure to promote heat transfer between the patient's body and the heat transfer liquid. The compliant support is adapted to underlie and generally conform to the shape of the portion of the patient's body to define a well adjacent to the patient's body portion for accumulating heat transfer liquid. A liquid delivery system drives the heat transfer liquid into the enclosure.

In another aspect, the apparatus generally comprises a support adapted to define an enclosure for receiving the portion of the patient's body therein. The support being constructed to conduct a heat transfer liquid into direct contact with the portion of the patient's body received in the enclosure to promote heat transfer between the patient's body and the heat transfer liquid. A cover is selectively moveable between a first position in which the cover generally covers the patient, and a second position in which the cover is not covering the patient. A liquid delivery system drives the heat transfer liquid into the enclosure. The liquid delivery system is operable with the cover in the first position, and operable with the cover in the second position.

In still another aspect, the present invention is directed to a method for adjusting the body temperature of a patient. The method generally comprises enclosing at least a portion of a patient's body within an interior space of an enclosure. The enclosure has an inlet for receiving a heat transfer liquid into the interior space, and an outlet in fluid communication with the interior space of the enclosure for exhausting the heat transfer liquid from the enclosure. In addition, the method includes directing the heat transfer liquid through the inlet of the enclosure into the interior space for flow over the patient's body in direct liquid contact therewith to promote heat transfer between the patient's body and the heat transfer liquid to the outlet of the enclosure. The method also includes directing a heat transfer gas into the interior space for flow over the patient's body in direct contact therewith to promote heat transfer between the patient's body and the heat transfer gas.

In yet another aspect, the method generally comprises filling a pneumatic support with a fluid for supporting and substantially underlying a portion of the patient's body. In addition, the method includes enclosing at least a portion of a patient's body within an interior space at a location overlying the pneumatic support. The method also includes directing a heat transfer liquid into the interior space of the enclosure for flow over the patient's body in direct liquid contact therewith to promote heat transfer between the patient's body and the heat transfer liquid.

In still another aspect, the method generally comprises enclosing at least a portion of a patient's body within an interior space of an enclosure. The enclosure has an inlet for receiving heat transfer liquid into the interior space, and an outlet in fluid communication with the interior space of the enclosure for exhausting the heat transfer liquid from the enclosure. In addition, the method includes directing the heat transfer liquid through the inlet of the enclosure into the interior space for flow over the patient's body in direct liquid contact therewith to promote heat transfer between the patient's body and the heat transfer liquid to the outlet of the enclosure. The method also includes maintaining a predetermined height of heat transfer liquid in the enclosure.

Other objects and features will be in part apparent and in part pointed out hereinafter.

BRIEF DESCRIPTION OF THE DRAWINGS

FIG. 6 is a section on line 6-6 of FIG. 2 but with the patient removed;

FIG. 7 is an enlargement of a passage formed in the cover shown in FIG. 6;

Corresponding reference characters indicate corresponding parts throughout the several views of the drawings.

DETAILED DESCRIPTION OF THE PREFERRED EMBODIMENT

Figure 1:
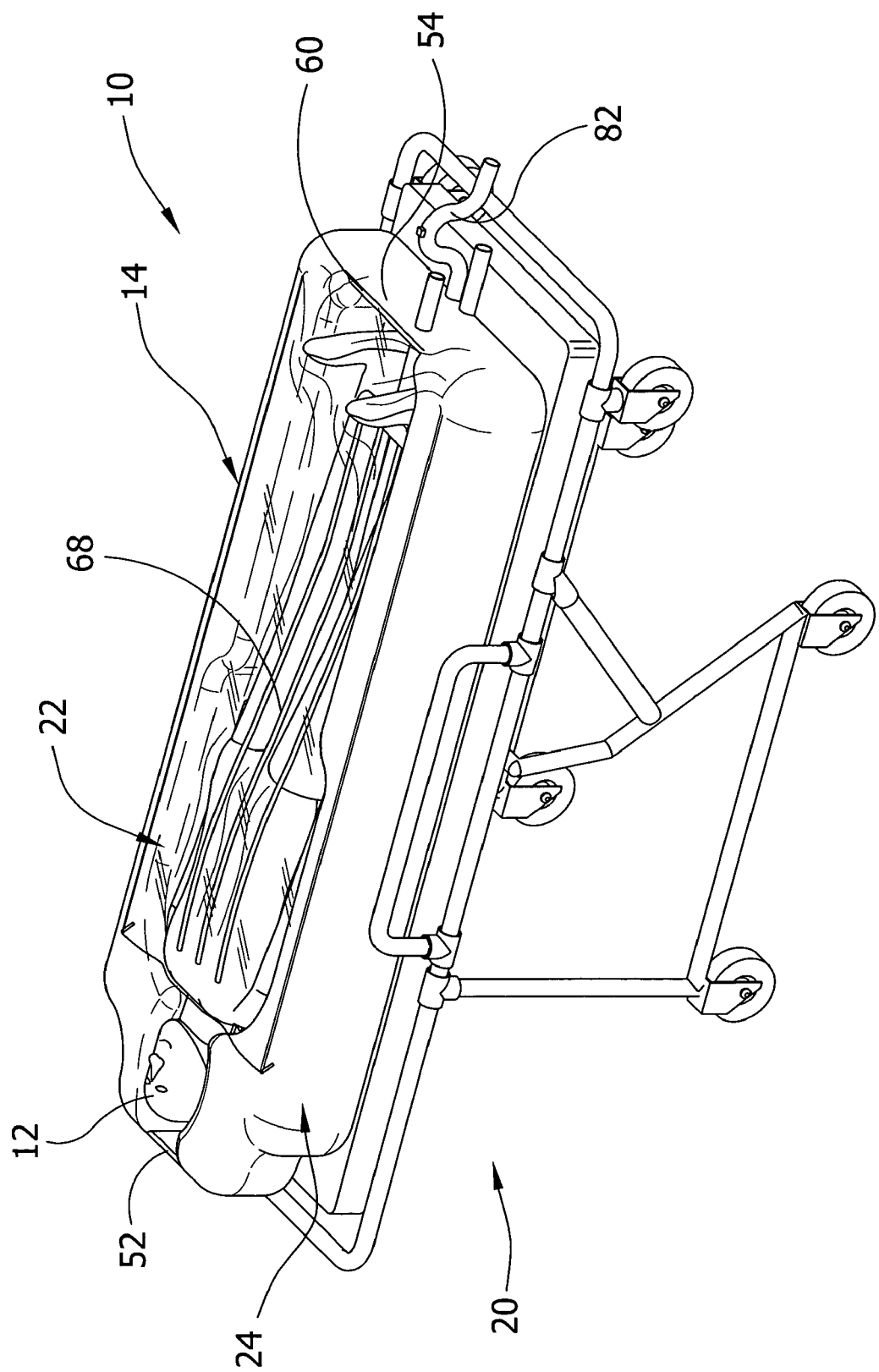
FIG. 1 is a perspective of an apparatus of the present invention for altering the body temperature of a patient, the apparatus being positioned on a gurney.
Figure 2:
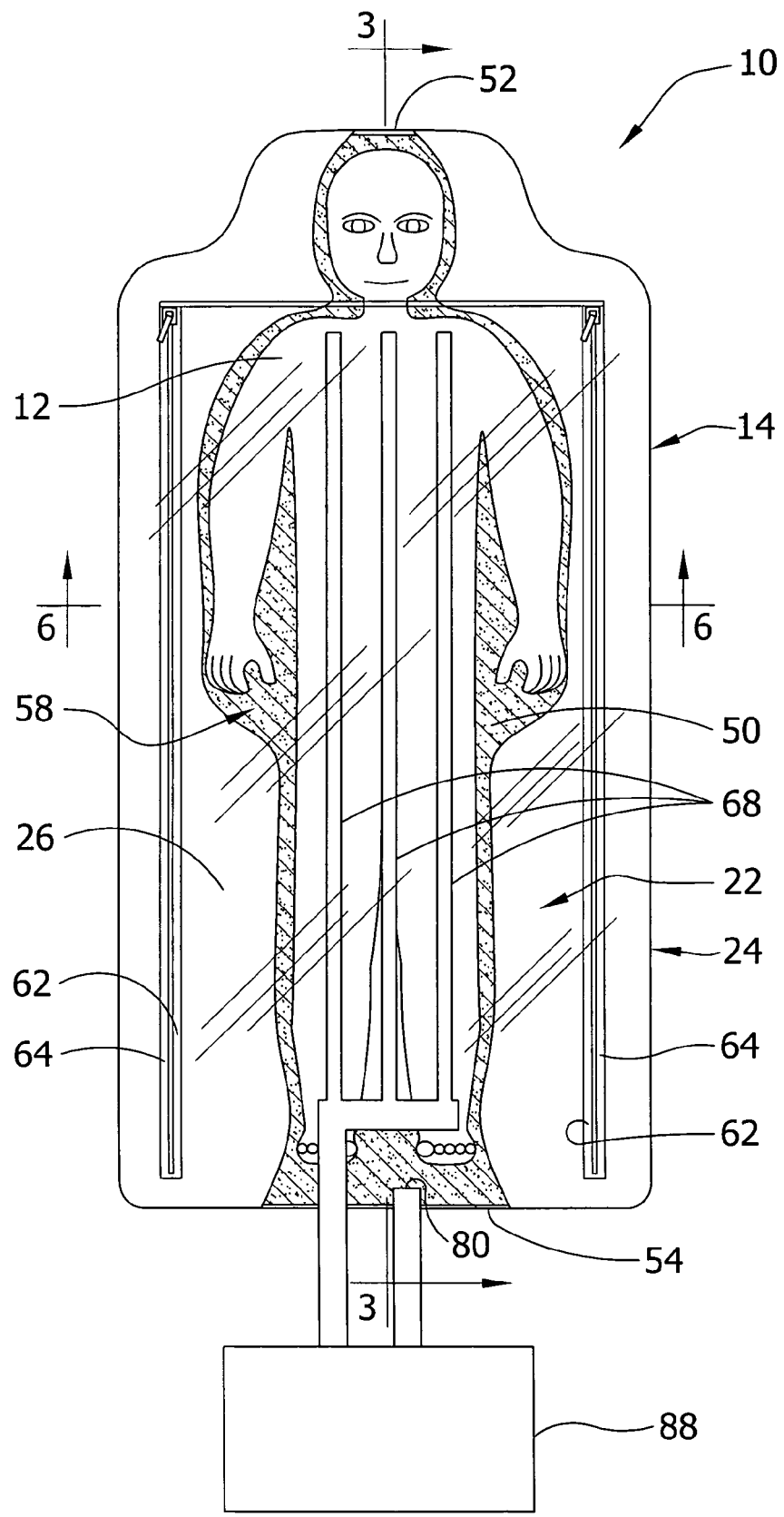
FIG. 2 is a top plan of the apparatus removed from the gurney.

Referring now to the drawings and particularly to FIGS. 1 and 2, reference number 10 generally indicates an apparatus for adjusting the body temperature of a patient 12. The apparatus 10 generally comprises an enclosure, indicated at 14, defining an interior space 16 (FIG. 5) for receiving at least a portion of a patient's body. While it is understood that any portion of the patient's body (including the entire body) may be placed inside the enclosure 14, for exemplary purposes, the illustrated portion of the patient's body received in the interior space 16 of the enclosure 14 is the patient's body from the neck downward, including the torso, arms, and legs. The enclosure 14 is adapted to generally conform to the shape of the patient's body received therein to accommodate patients of various shapes and sizes. For example, in one configuration, the enclosure 14 is suitable for individuals having a size between about the 5$^{th}$ percentile and about the 95$^{th}$ percentile adult male. Enclosures adapted to receive smaller individuals (e.g., babies, children, small adults) or larger individuals are also contemplated.

The enclosure 14 is also adapted to allow heat transfer liquid 18 (FIG. 12), such as water, saline or other suitable liquids, or heat transfer gas 116 (FIG. 14) to flow into the interior space 16 for direct contact with the patient's body to promote heat transfer between the patient 12 and the heat transfer fluid. To raise the temperature of a patient 12, the heat transfer fluid is directed into the interior space 16 of the enclosure 14 at a temperature greater than the temperature of the portion of the patient's body. For example, the heat transfer fluid may have a temperature in a range of about 43° C. (109° F.) to about 47° C. (117° F.), such as about 45° C. (113° F.). One application of such a warming enclosure would be to warm a patient 12 suffering from unintended hypothermia.

To lower the temperature of a patient 12, the heat transfer fluid is directed into the enclosure 14 at a temperature lower than the temperature of the body portion of the patient received in the interior space 16 of the enclosure so that the fluid cools the body portion of the patient. For example, the heat transfer fluid may have a temperature in a range of about 0.5° C. (34° F.) to about 4° C. (36° F.). Heat transfer fluid introduced into the enclosure 14 at such a temperature has been found to cool the body at a sufficient rate to induce hypothermia while minimizing any adverse effects to the skin of the patient. It is to be understood that temperatures other than those listed above can be used to adjust the temperature of a patient 12 received in the interior space 16 of the enclosure 14.

As mentioned above, hypothermia can be used to minimize or prevent damage to vital organs, including the brain, caused by cardiac arrest. It is well recognized that organ damage can, and typically does, occur shortly after the victim has suffered cardiac arrest. As a result, it is often in the victim's best interest to quickly and effectively induce hypothermia to minimize or prevent organ damage. Since many victims of cardiac arrest are initially treated by first responders (i.e., police officers, firefighters, emergency medical technicians), in one configuration, the apparatus 10 is portable for use remote from a medical facility. Moreover, the enclosure 14 is sized and shaped for placement on a stretcher, such as an ambulance or emergency gurney (generally indicated at 20), to facilitate the transportation of the patient 12 to a medical facility in a conventional manner while placed in the enclosure (FIG. 1). Accordingly, the enclosure 14 may have a width between about 66 centimeters (26 inches) and about 76 centimeters (30 inches) and a length between about 203 centimeters (80 inches) and about 210 centimeters (83 inches), the approximate range of dimensions for a standard ambulance or emergency gurney 20. It is contemplated that the enclosure 14 may have other configurations without departing from the scope of this invention. It is also contemplated that the enclosure 14 may be used to treat other medical conditions or have application in other medical procedures (e.g., hyperthermia, trauma, stroke, heart attack, enhancements of anti-cancer therapies, surgical support, and general thermal management). Moreover, although the patient 12 is most commonly a human, the apparatus 10 could be used for other animals.

Figure 3:
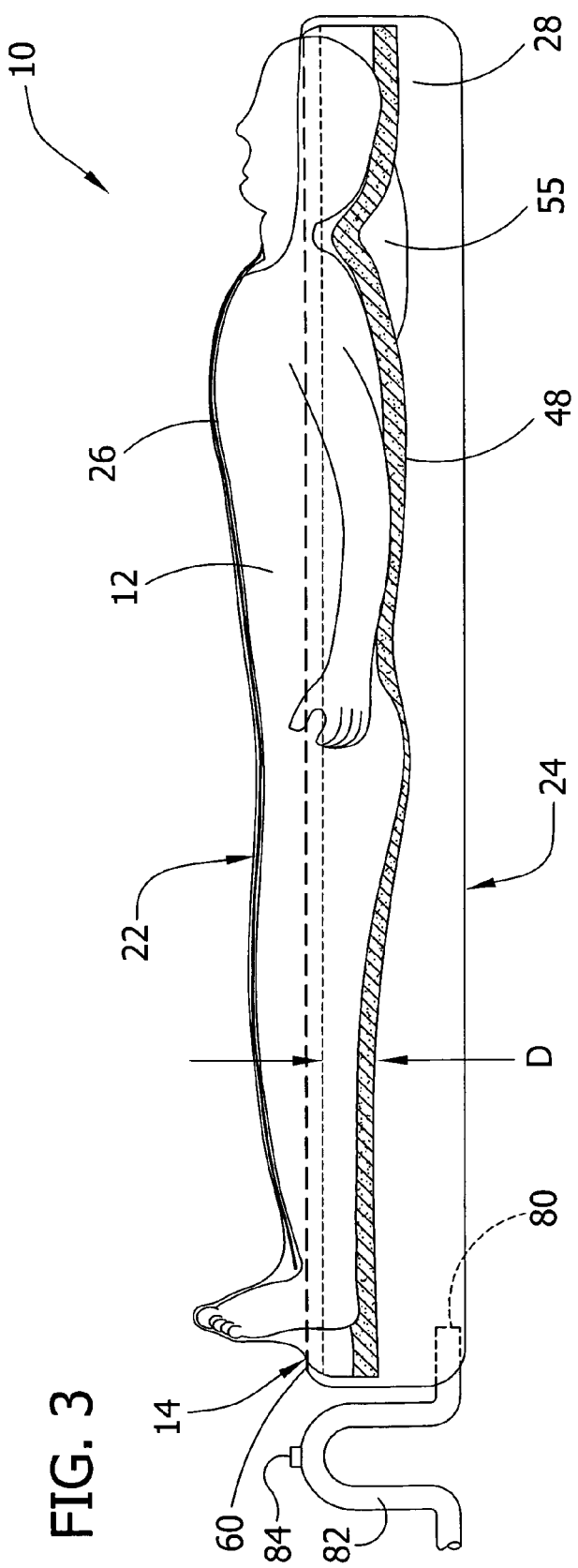
FIG. 3 is a section of the apparatus on line 3-3 of FIG. 2.

The amount of time necessary to induce hypothermia in a patient 12 is dependent on numerous factors including the portion of the patient received in the interior space 16 of the enclosure 14, the temperature of the heat transfer fluid, and the amount of time the heat transfer fluid is in contact with the portion of the patient's body. As a result, in one configuration, the enclosure 14 is adapted to enclose the patient's body from the neck down thereby providing a large portion of the patient's total surface area for heat transfer with the heat transfer fluid. As illustrated in FIG. 3, the enclosure 14 comprises a cover, indicated at 22, for overlying the patient 12 from the neck downward, and a compliant support, indicated at 24, for underlying the patient's entire body.

As shown in FIGS. 2 and 3, the cover 22 comprises a limp sheet-like member 26 adapted to generally conform, under its own weight, to the contours of the patient 12 which it is covering. The sheet-like member 26 is preferably made of a transparent material such as polyvinyl chloride (PVC), polyethylene, or polyurethane so that the body of the patient received within the enclosure can be viewed. It is understood that a sheet-like member (not shown) may be made of a non-transparent material or has a portion that is transparent with the remainder of sheet-like member being non-transparent. In another configuration (not shown), the cover 22 further comprises a porous layer disposed between the sheet-like member 26 and patient's body. The porous layer, such as batting or open-celled foam, supports the sheet-like member 26 in a position spaced from the patient's body thereby providing a fluid passageway for allowing the heat transfer fluid to pass between the sheet-like member and the patient's body.

Figure 4:
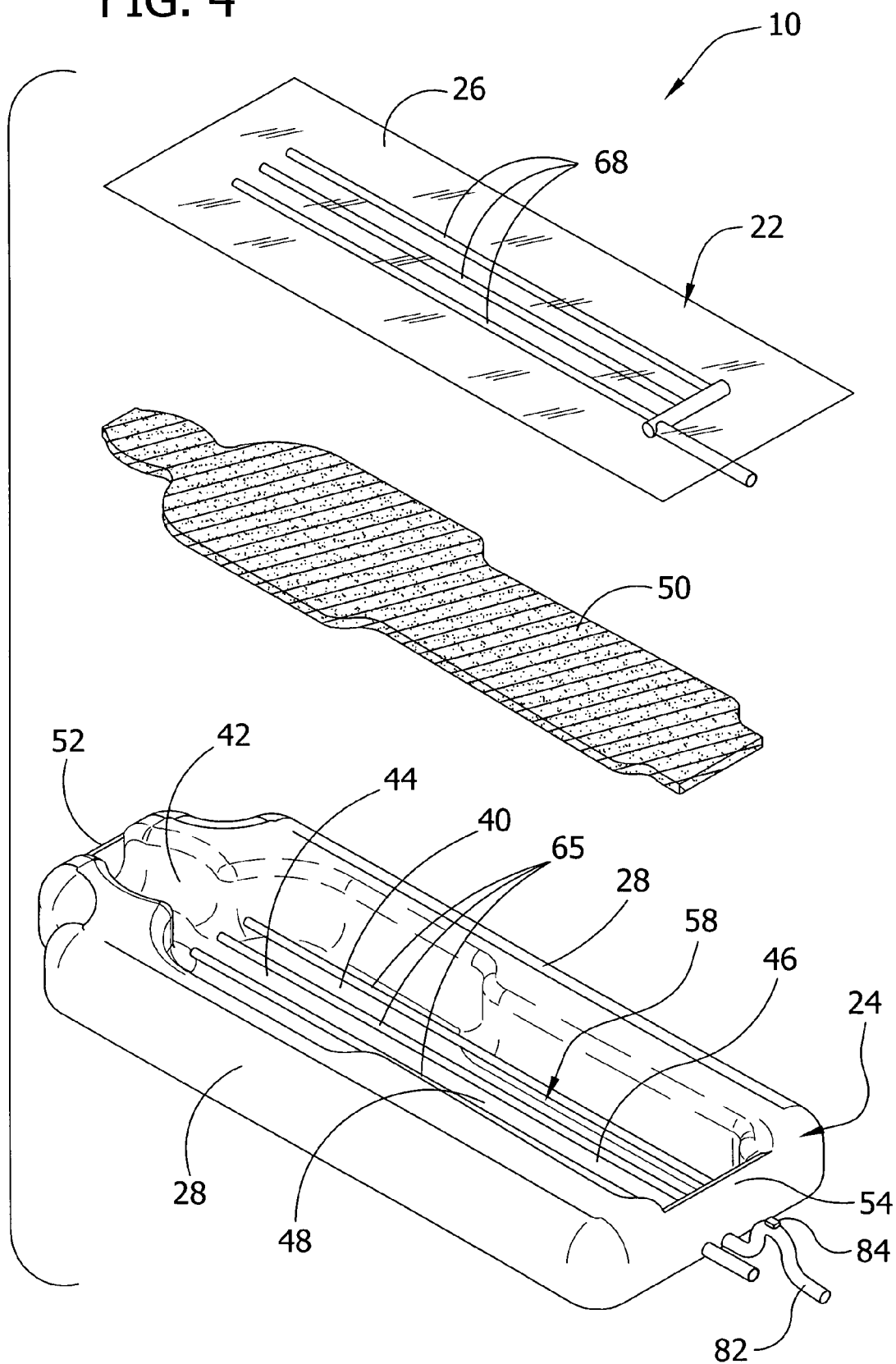
FIG. 4 is an exploded perspective of the apparatus.
Figure 11:
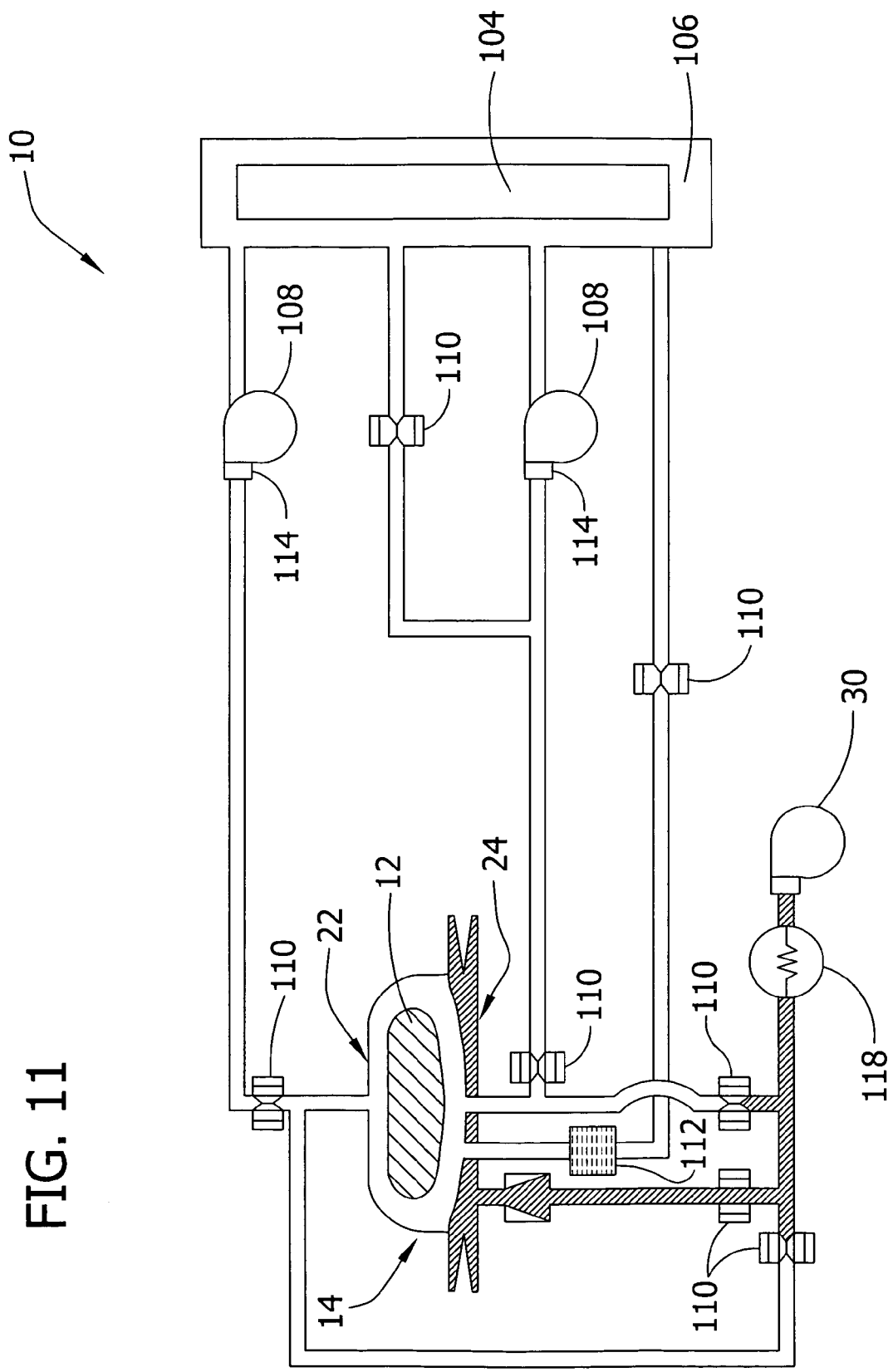
FIG. 11 is a schematic of the apparatus of the present invention showing an air pump pumping air into the compliant support.
Figure 17:
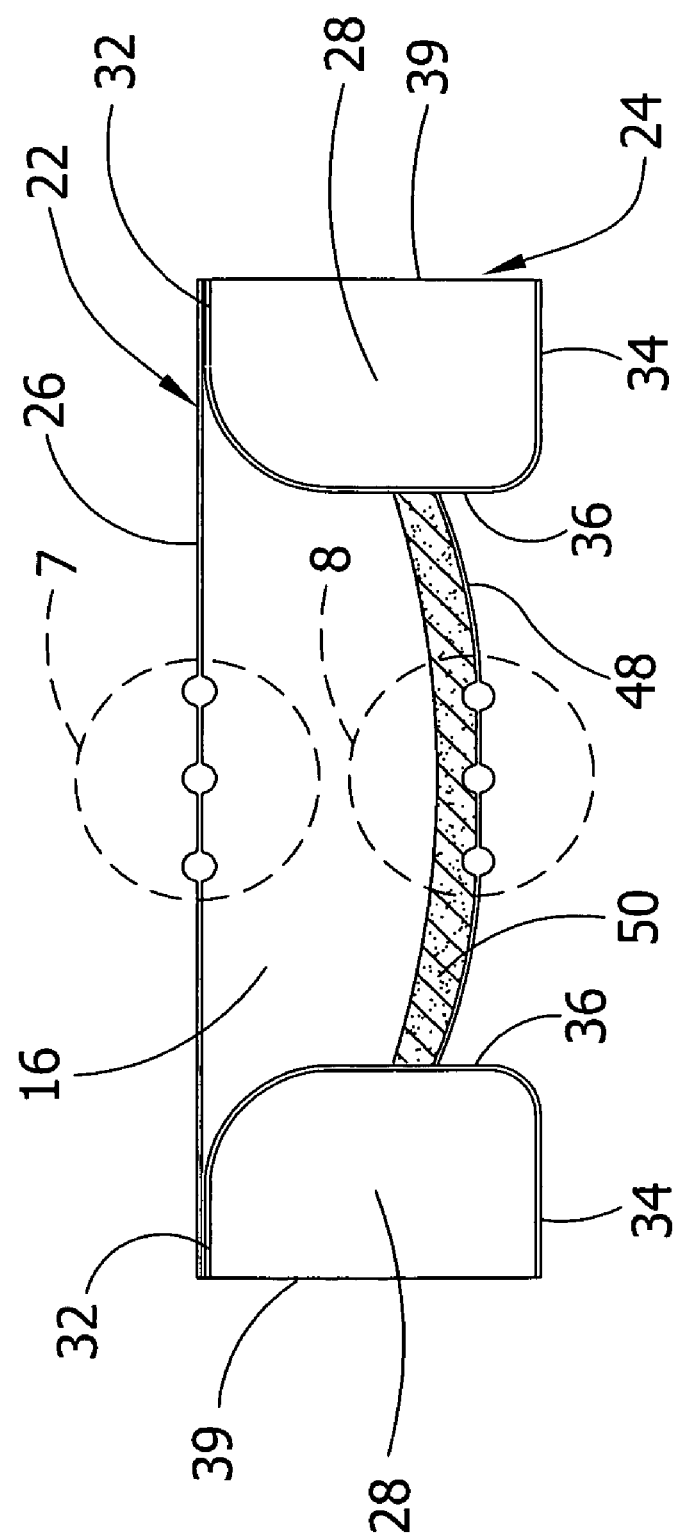
FIG. 17 is a section similar to the one shown in FIG. 6 but with a different tube configuration.

The compliant support 24 is a pneumatic support, which, like the cover 22, also generally conforms to the shape of the patient's body when the body rests on the support. Moreover, the compliant support 24 minimizes pressure concentrations beneath the patient 12 which facilitates flow of heat transfer fluid beneath the patient and minimizes the possibility of pressure sores developing in the skin of the patient. The compliant support 24, as illustrated in FIG. 4, comprises two generally elongate, gas-filled tubes 28, which form a right side and a left side of the support. As illustrated in FIG. 11, the gas-filled 28 tubes are selectively inflatable using an air pump 30 (or manually) and deflatable by bleeding the air from the tubes. Referring now to FIG. 6, each of the tubes 28 has a top 32, a bottom 34, an interior facing side 36, and an exterior facing side 38. The interior facing sides 38 are generally shaped to conform to the side profile of the patient 12. Accordingly, the tubes 28, when inflated, collectively define a recess 40 in a center of the support 24 (i.e., between the gas-filled tubes 28) for receiving the patient's body (FIG. 4). More specifically, the tubes 28 generally conform to the sides of the patient 12 as they are being inflated thereby forming a pocket 42 sized and shaped for receiving the head and neck of the patient, a broader region 44 for receiving the torso of the patient, and a tapered pocket 46 for receiving the legs and feet of the patient. The pocket 42, which is adapted for receiving the head and neck of the patient 12, is configured to support the head in an upward-facing direction thereby maintaining the patient's breathing passageways (i.e., nose and mouth) out of contact with the heat transfer fluid in the interior space 16 of the enclosure 14. The pocket 42 prevents the patient's head from moving to a side-facing direction. The tubes 28 may be captured on their exterior facing sides 38 (to define the outer perimeter of the support) by a restraint 39 made of a rigid material, such as a rigid plastic, to thereby limit outward expansion of the tubes (FIG. 17). The restraint 39 shown in FIG. 17 is integral with the support 24 (i.e., forms one wall of the support). However, it is contemplated that the restraint may be formed as a separate component. In another configuration (not shown), the restraint 39 may be a tether or a plurality of tethers extending between the interior walls of the tubes 28. The restraint 39 provides added support to the tubes which allows the tubes 28 to hold their shape under loads from the heat transfer liquid 18 and the patient's body weight. It is understood that the compliant support 24 may have different shapes and sizes or be conformable with the patient's body in a way different from that described herein. For example, the compliant support 24 could be filled with any suitable fluid, including a liquid, or any suitable flowable material, such as polystyrene beads.

With reference to FIGS. 4 and 6, a liquid impermeable sheet-like member 48 extends between the generally opposing portions of the tubes 28, and a porous layer 50 overlies the member. The impermeable member 48 is attached to the tubes 28 such that the member slopes from the head pocket 42 of the enclosure 14 toward the tapered foot pocket 46. The impermeable member 48 retains the heat transfer fluid within the enclosure 14, while a porous layer 50, such as rich loft polyester batting or an open-cell polyurethane foam, allows heat transfer fluid to pass into contact with the patient's body portion for flow across the skin throughout the enclosure. The impermeable member 48 comprises a transparent material such as PVC, polyethylene, or polyurethane. It is understood that the impermeable member 48 may comprise in its entirety a non-transparent material or have a portion that is transparent with the remainder of impermeable member being non-transparent. It is also understood that the impermeable member 48 may be attached to the tubes such that the impermeable member lies in a generally horizontal plane or is sloped from the foot pocket 46 toward the head pocket 42.

Referring again to FIG. 4, a front end panel 52 and a rear end panel 54 extend between the tubes 28 and define the forward and rearward extent of the support 24. The end panels 52, 54 can be made for a variety of materials, such as semi-rigid plastic, plastic foam, elastic plastic sheeting, an inflatable section, or a constrained inflatable section (e.g., a series of inflatable tubes bonded to one another).

The compliant support 24 further comprises a positioner 56 (FIG. 5), such as a head rest, a forehead strap, or indicia printed on the support, that indicates to the user where to properly place the patient 12 on the compliant support. The indicia may be text (such as written instructions), an outline of a body or portion thereof, or an image, such as an image of a face. It is contemplated that the positioner 56 may be placed anywhere on or in the enclosure.

As illustrated in FIG. 3, the compliant support 24 may further comprise a selectively inflatable head rest 55, which not only provides the user with an indication where to position the patient 12, but also maintains the patient's breathing passageways (i.e., nose and mouth) in spaced relation with the heat transfer fluid in the interior space 16 of the enclosure 14. Moreover, the head rest 55 angles the patient's head back thereby opening the patient's breathing passageways. Thus, the head rest 55 places the patient's head in a position suitable for mouth-to-mouth resuscitation, one of the steps in performing CPR. In another configuration (not shown), the head rest 55 provides a pillow for the patient's head to rest. As a result, the patient's head is angled forward which may necessitate the use of a breathing tube to assist the patient with breathing. Thus, the patient's head can be positioned generally flat, angled forward, or angled back thereby providing the user the option to select the position best suited for a particular patient 12. It is understood that the head rest 55 may be formed from a non-inflatable component. It is also understood that the head rest 55 may be integral with the compliant support 24 or formed as a separate component.

The end panels 52, 54, impermeable member 48, and gas-filled tubes 28 of the compliant support 24 are collectively configured to form a watertight well, generally indicated at 58, in the center of the compliant support for receiving the entire body of the patient 12. The patient 12 is positioned in a supine position on the impermeable member 48 with the tubes 28 in a deflated state. The tubes 28 are then inflated to conform the interior side walls 36 of the tubes to the portion of the patient's body juxtaposed thereto. The tubes 28 provide longitudinally extending walls to prevent heat transfer fluid 18 from leaking in a lateral direction. The end panels 52, 54 prevent the heat transfer fluid 18 from leaking in a longitudinal direction, and the impermeable member prevents the heat transfer fluid from leaking in the downward direction. It is understood that the impermeable member may also extend over the tubes and end panels thereby preventing leaking in all directions.

As a result, the well 58 is sized and spaced to generally conform to the patient's body received in the interior space 16 of the enclosure 14. Thus, the volume of heat transfer fluid necessary to effectively alter the temperature of the patient 12 is also dependent on the size and shape of the patient. For example, a larger patient will require more heat transfer fluid than will a smaller patient to achieve a similar rate of heat transfer. Moreover, the heat transfer fluid within the interior space 16 of the enclosure 14 is maintained in a relatively thin layer and near or in contact with the patient's body positioned the well 58. As a result, the amount of heat transfer liquid 18 necessary to effectively alter the temperature of the patient 12 can be minimized. This becomes increasingly important in remote areas where volumes of heat transfer liquid 18, which can become heavy, need to be carried by hand. For example, about 16 liters (4.2 gallons) of heat transfer liquid 18 would weigh about 16 kilograms (35 pounds) where as about 12 liters of heat transfer liquid would weigh about 12 kilograms (27 pounds).

The well 58 enables heat transfer between the underside and side of the patient's body by allowing heat transfer fluid 18 to accumulate under and adjacent to the patient's body, and allowing heat transfer fluid to be delivered to the patient's body from a location beneath the patient 12. The depth D of the well 58 is varied along a longitudinal axis of the enclosure (FIG. 3). The well 58 is deeper in the region receiving the torso of the patient 12 than in the regions receiving the head, legs, and feet since a large portion of the patient's weight is contained in the torso. The well 58 has a depth D between about 2.5 centimeters (1 inch) and about 20 centimeters (8 inches), and preferably between about 12.7 centimeters (5 inches) and about 15 centimeters (6 inches) in the region adapted to receive the torso. These depths correspond generally to about one-half of the chest heights of adult males between the $5^{th}$ percentile and $95^{th}$ percentile. This variation in well 58 depths allows more heat transfer liquid to accumulate around the torso of the patient, a region of the body amenable to heat transfer, than with the head, legs, and feet of the patient 12. The reasons for managing the depth of the heat transfer liquid 18 in the region adapted to receive the head of the patient are apparent. It is understood that the well 58 can have a generally uniform depth D or have depths different from those indicated, such as when the enclosure 14 is designed for use with smaller or larger adults, children, or babies, without departing from the scope of this invention.

Figure 5:
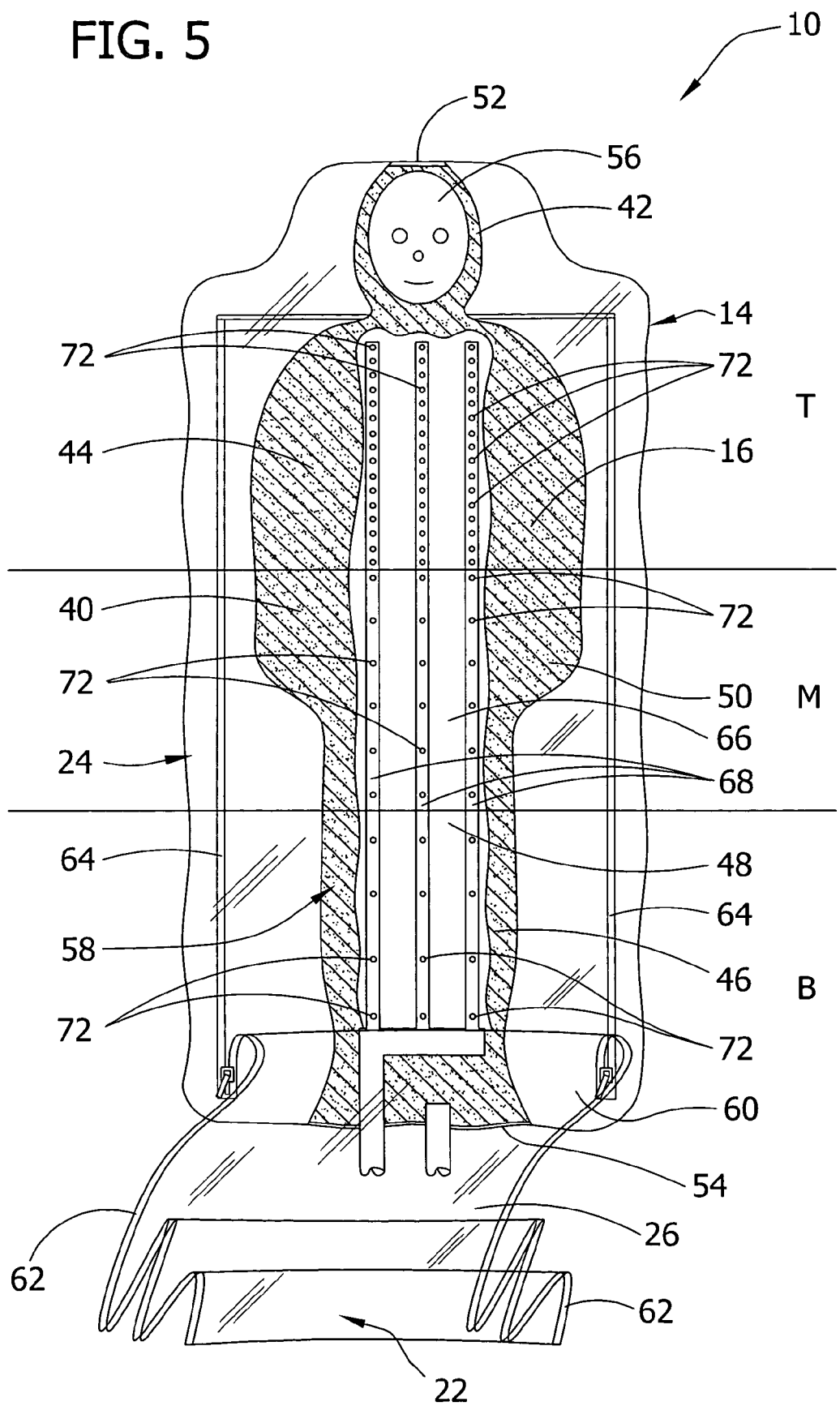
FIG. 5 is a top plan of the apparatus with a cover pulled back and a porous layer partially cut away thereby exposing a passage.

As depicted in FIGS. 2 and 5, the cover 22 and the compliant support 24 are adapted for sealing engagement with each other. The cover 22 is hinged to the support along an edge 60 of the support 24 to ensure that the cover and support remain attached and properly aligned for use with respect to one another. As illustrated, the cover 22 includes two first sealing portions 62 and the support 24 includes two second sealing portions 64 for engaging with the first sealing portions 62. One pair of sealing portions (i.e., one first sealing portion 62 and one second sealing portion 64) extends longitudinally adjacent the right side of the enclosure 14, and the second pair of sealing portions 62, 64 extends longitudinally adjacent the left side of the enclosure 14. In another configuration (not shown), the sealing portions 62, 64 are joined along edge 60 thereby providing a continuous seal for allowing the cover 22 to be completely removed from compliant support 24. The sealing portions 62, 64 comprise slide fastener members, such as the FLEXI-GRIP® 7 manufactured by MiniGrip/ZIP-PAK®, an ITW Company, of Orangeburg, N.Y., USA, which are selectably sealingly engageable with one another. In another configuration (not shown), the sealing portions 62, 64 comprise a hook and loop fastening system. For example, a strip of hook material may be adhered to the compliant support 24, and a strip of loop material adhered to the cover 22 for engaging the hook material located on the compliant support. It is understood that the loop material can be placed on the compliant support 24 and the hook material on the cover 22.

The cover 22 is slightly smaller than the support 24 which allows the sealing portions 62, 64 of both the cover and the compliant support to lie above and laterally inward from the sides of the support. As a result, the sealing portions 62, 64 are positioned away from the medial line of the patient 12 received in the interior space 16 of the enclosure 14 thereby allowing CPR to be administered to the patient without interference from the sealing portions. Furthermore, the sealing portions 62, 64 are positioned on a portion of the enclosure that is maintained generally horizontal. As a result, the potential for the sealing portions 62, 64 to be bent or otherwise deformed is minimized. Bending and deformation of the sealing portions 62, 64 may diminish the ability to seal or to be opened or closed. Moreover, the sealing portions 62, 64 are positioned at a location above the depth D at which heat transfer liquid 18 accumulated in the well 58 of the compliant support 24, which reduces the demand on the sealing portions (i.e., the sealing portions do not have to form water tight seals). Lastly, the sealing portions 62, 64 are conveniently located for a user thereby providing the user with easy access to the patient 12.

Figure 8:
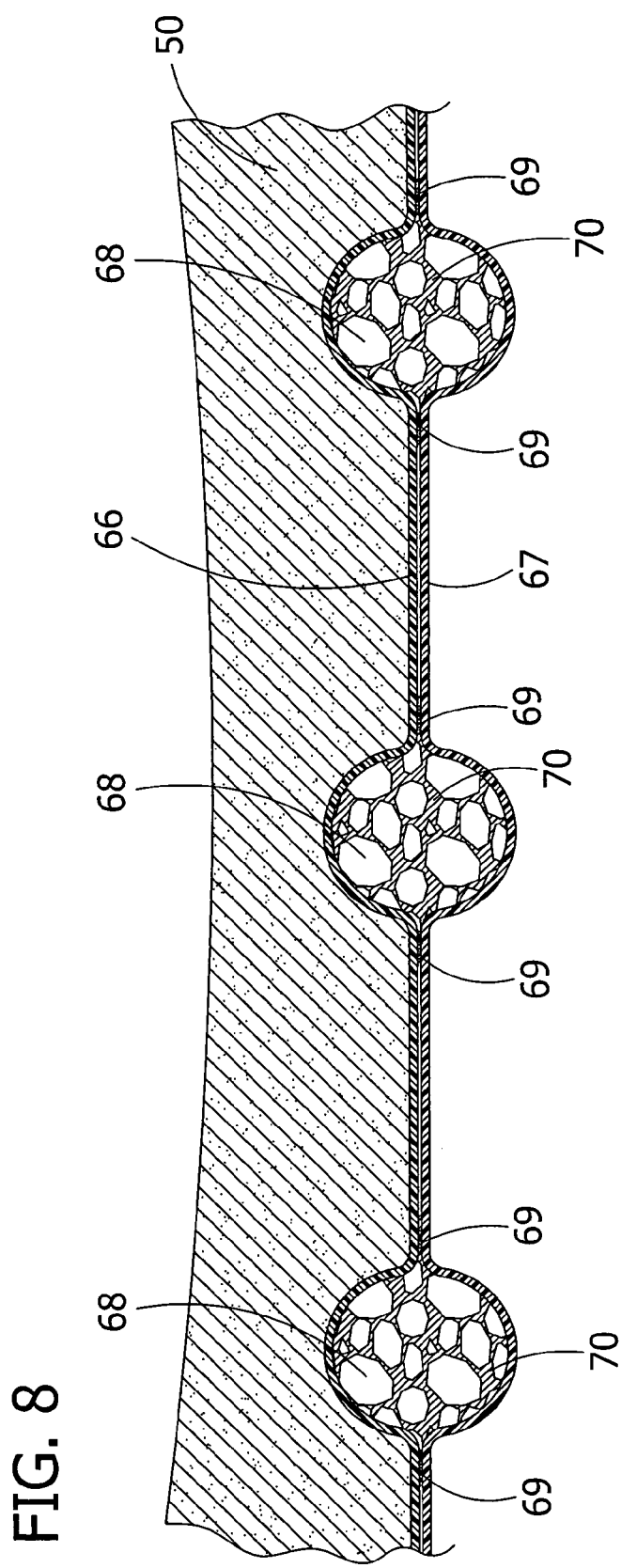
FIG. 8 is an enlargement of the passage in a compliant support shown in FIG. 7.

With reference to FIGS. 6 through 8, both the impermeable member 26 of the cover 22 and the impermeable member 48 of the compliant support 24 include a flexible sheet-like body-facing component 66 and a flexible sheet-like outer component 67 that are adapted for face-to-face engagement with one another. The body-facing and outer components 66, 67 are liquid impermeable and joined to one another along their facing sides to form at least one passage 68 therebetween for the heat transfer fluid (FIGS. 2 and 5). Heat sealing is used to seal the components together along a seam 69 to form the passage 68 because it provides adequate strength without requiring additional raw materials. Other methods of forming the passages 68 or sealing the components 66, 67 to one another, such as adhesives, are also contemplated as being within the scope of the present invention. The passages 68 have a length approximately equal to the length of the cover 22, a width of approximately 25 mm, and a height of approximately 3 mm. It is understood that the dimensions provided for the passages 68 are exemplary only and that the passages can be formed to have various dimensions.

The passages 68 are configured to distribute fluid over a large portion of the surface area of the patient's body. As shown in FIGS. 2 and 5, the passages 68 comprise three passages extending generally longitudinally of the enclosure in each the impermeable member 26 of the cover 22 and the impermeable member 48 of the compliant support 24. Accordingly, three of the six total passages 68 are disposed above the patient's body while the other three passages are disposed beneath the patient's body. At least two of the passages 68 are arranged to engage the patient's body at a position offset from the medial line of the patient's body. This feature is particularly useful where CPR is to be administered to the patient 12, because chest compressions occur generally along the medial line of the patient. Where the patient 12 is placed within the enclosure 14 and the passage 68 corresponds approximately with the medial line of the patient, chest compressions may repeatedly block the flow of heat transfer fluid through the passage, thereby reducing fluid flow through the enclosure 14. Where at least some of the passages 68 are offset from the medial line of the patient 12, chest compressions performed in rendering CPR treatment are less disruptive of fluid flow through the enclosure 14. Other configurations of the passages 68 are also contemplated as being within the scope of the present invention. It is understood that the cover 22 and compliant support 24 may have more or fewer passages 68 without departing from the scope of this invention. It is also understood that the cover 22 may have a different number of passages than the compliant support 24. For example, the cover 22 could have about seventeen passages 68 closely spaced together with each passage having a width of approximately 1.2 centimeters (0.5 inches). In this configuration, the compliant support 24 could also have seventeen passages 68, more than seventeen passages, or fewer than seventeen passages. The passages 68 in the compliant support 24 could also be wider or narrower than the passages in the cover 22.

Referring now to FIG. 8, the passages 68 formed in the impermeable member 48 of the compliant support 24 are each supported by a hold-open 70, which holds the passage open and permits flow of the heat transfer fluid through the passage past the hold-open. The hold-opens 70 provide the rigidity necessary to maintain the passages 68 open even when subjected to a load, such as the weight of the patient's body which bears on the passages 68 formed in the impermeable member 48 of the support 24. The hold-open 70 may be a porous material, such as open-celled foams, particulate matter (e.g., polystyrene beads), batting, non-woven materials, or mechanical devices, such as coil springs. One suitable open-celled foam is a reticulated polyurethane foam having approximately 25 pores per inch manufactured by Foamex of Eddystown, Pa., USA, and sold under the trade name SIF®.

The passages 68 formed in the impermeable member 26 of the cover 22 are free of hold-opens 70 (FIG. 7). As a result, before the passage 68 fills with heat transfer fluid, the sheet-like body-facing component 66 and sheet-like outer component 67 of the passage generally lie flat against one another. Once heat transfer fluid flows inside the passage 68, the cross-sectional area of the passage increases to allow fluid to flow between the components. It is to be understood that the passages 68 formed in impermeable member 48 of the compliant support 24 may be substantially free of hold-opens 70 and the passages 68 formed in the cover 22 may have hold opens.

Referring again to FIGS. 5 and 6, the body-facing component 66 of both the cover 22 and the compliant support 24 have at least one opening 72 (i.e., an inlet) therein corresponding to the passage 68 for allowing the heat transfer fluid to pass from the passage to the porous layer 50 situated between the body-facing component 66 and the portion of the patient's body. Each inlet 72 is generally circular and preferably has a diameter of about 1 millimeter (0.04 inches). The small diameter inlets 72 restrict the flow of heat transfer fluid from the passage 68 into the enclosure 14 thereby causing the entire length of the passages to fill with heat transfer fluid. Thus, the heat transfer fluid is evenly distributed via the passage 68 to each of the inlets 72. The body-facing components 66 of the impermeable member 26 of the cover 22 and the impermeable member 48 of the compliant support 24 are disposed above and below the patient's body, respectively, thereby arranging the inlets 72 on opposite sides of the patient. As shown in FIG. 5, the body-facing component 66 of the impermeable member 48 of the support 24 has a plurality of inlets 72. The body-facing component 66 of the impermeable member 26 of the cover 22 also has a plurality of inlets (not shown) arranged in a similar manner to the inlets 72 of the compliant support 24.

The number of inlets 72 positioned in various portions of the enclosure 14 may be varied to regulate the distribution of heat transfer fluid throughout the enclosure. As illustrated in FIG. 5, the inlets 72 are positioned for evenly distributing the heat transfer fluid throughout the enclosure 14. However, it is understood that the inlets 72 may be positioned to distribute heat transfer fluid unevenly to the enclosure 14. By having an uneven flow distribution, a greater volume of heat transfer fluid can be directed to selected portions of the patient's body, such as those more amenable to heat transfer (i.e., the head, neck, torso) than other non-selected portions of the patient's body, which are also received in the enclosure 14.

As shown in FIG. 5, the passages 68 in the impermeable member 26 of the cover 22 and in the impermeable member 48 of the compliant support 24 extend through the rear end panel 54 located adjacent the bottom of the enclosure 14. As a result, heat transfer fluid directed through the passages 68 flows from a bottom section B (i.e., the lower one-third) of the enclosure 14, through a middle section M (i.e., the middle one-third) to a top section T (i.e., the top one-third). To even the flow distribution, the number of inlets 72 increases along the passage 68 in a direction away from the bottom section B of the enclosure. Thus, the middle section M has a greater number of inlets 72 than does the bottom section B, and the top section T has a greater number of inlets than does the middle section. In the illustrated configuration, each passage 68 is in fluid communication with four inlets 72 located in the bottom section B, six inlets located in the middle section M, and sixteen inlets located in the top section T. In another configuration (not shown), the diameters of the inlets 72 are varied along the passage 68 in a direction away from the bottom section B of the enclosure. Using this approach, inlets 72 having smaller diameters are positioned near the bottom sections B while inlets with progressively larger diameters are positioned in the middle and top sections M, T. It is understood that numerous inlet 72 configurations are possible to adequately distribute heat transfer fluid to the body of the patient 12 by varying the size, shape, and distribution of the inlets.

The enclosure 14 also comprises at least one large diameter (e.g., 2.5 centimeters (1 inch)) outlet 80 extending through the rear end panel 54 of the compliant support 24 for exhausting heat transfer fluid 18 from the enclosure 14 (FIG. 3). It is contemplated that the large diameter outlet 80 may be larger or smaller than 2.5 centimeters. The outlet 80 is sufficiently sized to allow heat transfer liquid 18 to be exhausted from the enclosure 14 by gravity at a rate equal to or greater than the rate at which the heat transfer liquid is being delivered to the interior space 16 of the enclosure 14 to thereby prevent the enclosure from overflowing. The enclosure 14 may have more than one outlet 80, the outlet may be positioned at other sections of the enclosure, and the outlet may have other sizes and shapes.

Figure 9:
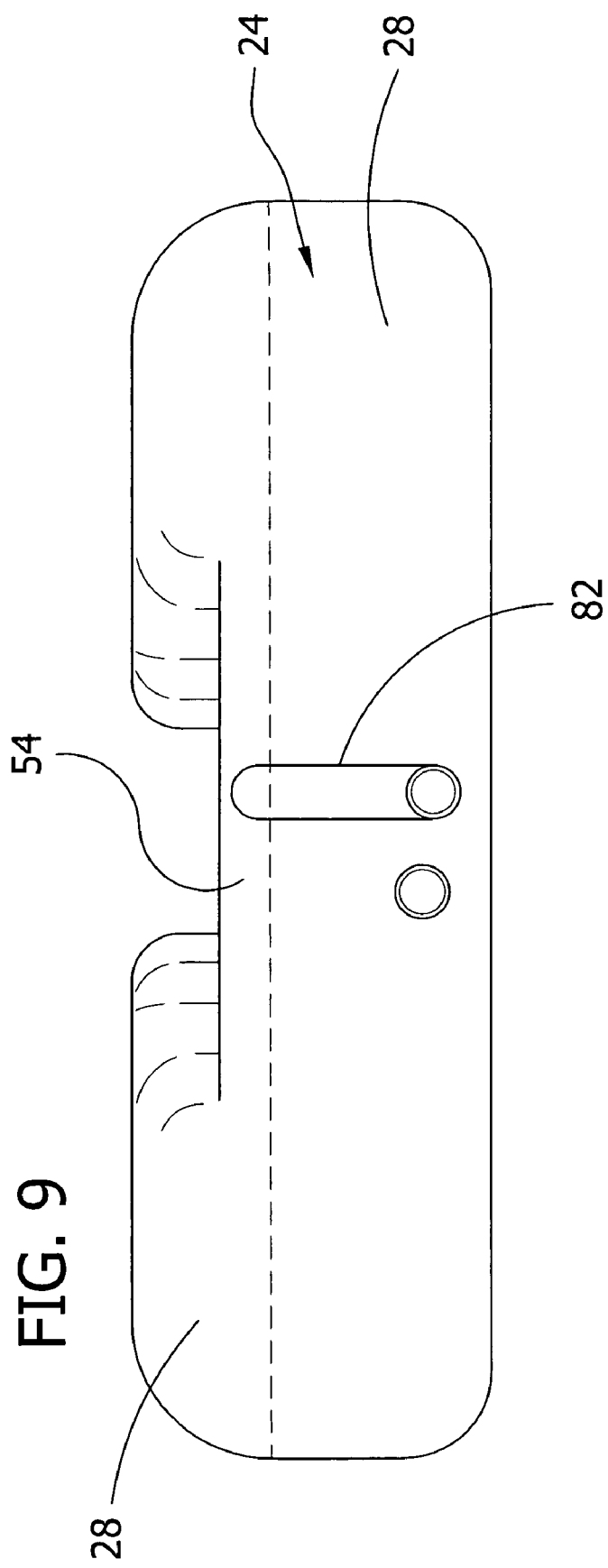
FIG. 9 is an end elevation of the apparatus showing a flow restrictor.

As shown in FIG. 3, an inverted U-shaped tube 82 (broadly, "a flow restrictor") is in fluid communication with the outlet 80 for maintaining the depth D of the heat transfer liquid 18 within the enclosure 14 at a predetermined level thereby allowing the heat transfer liquid to accumulate in the well 58 of the compliant support 24 adjacent and beneath the patient 12. The inverted U-shaped tube 82 has a predetermined height thereby creating a spillway which the heat transfer fluid must flow over before it is exhausted from the enclosure (See FIG. 9). For instance, if the heat transfer liquid 18 is maintained at a depth of between about 7 centimeters (2.8 inches) and about 15 centimeters (6 inches) in the enclosure 14, the tube 82 needs to have a height sufficient to prevent transfer liquid below the selected height from flowing through the outlet 80 and out of the enclosure. Since the tube 82 maintains fluid at a given height at the outlet 80 of the enclosure 14, it creates a positive gage pressure at the outlet of the enclosure, which would between about 0.69 kilopascals (0.1 pounds per square inch) and about 1.47 kilopascals (0.2 pounds per square inch) for an enclosure with a depth of heat transfer liquid between 7 centimeters (2.8 inches) and about 15 centimeters (6 inches). A vent 84 is positioned on the tube 82 to provide an air break to thereby prevent siphoning of the heat transfer liquid 18 from the enclosure 14. The vent 84 can be selectively closed to facilitate siphoning, which may be advantageous when the heat transfer liquid 18 is being exhausted from the enclosure 14. It is contemplated that the tube 82 may be transparent to view the level of heat transfer liquid 18 contained in the enclosure 14. It is understood that the flow restrictor may be a device besides an inverted U-shaped tube 82, such as an adjustable valve, without departing from the scope of this invention.

Figure 10:
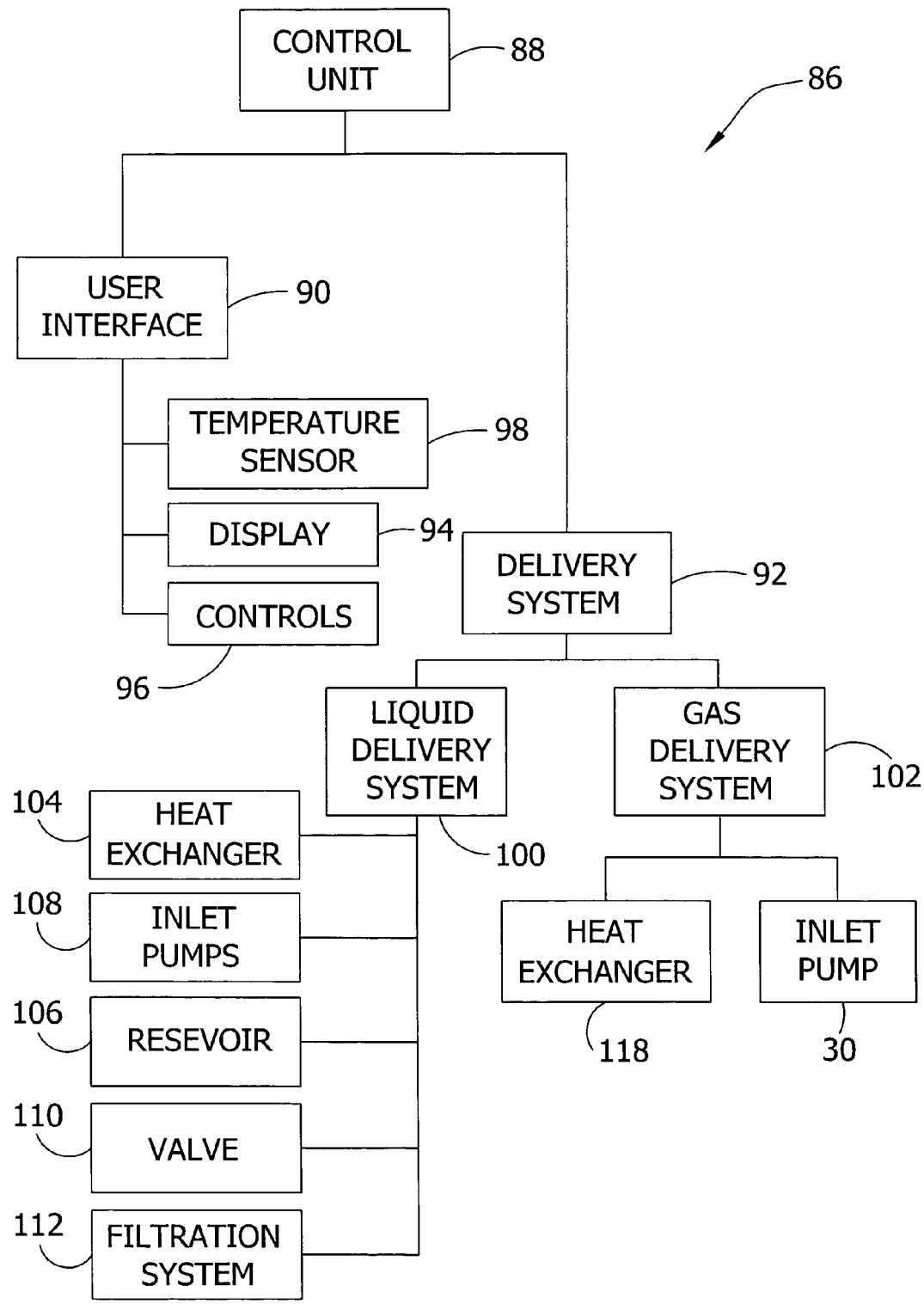
FIG. 10 is a schematic of a control system of the apparatus of the present invention.

Referring now to FIG. 10, the apparatus further comprises a control system, generally indicated at 86, for controlling operation of the apparatus 10. The control system 86 includes a control unit 88 having a user interface 90, and a delivery system 92. The user interface 90 includes a display 94 for visually indicating particular parameters of the control system 86, controls 96 that allow the user of the system to selectively control particular system functions, and one or more temperature sensors 98 for measuring the temperature of the patient 12. For example, the controls 96 may allow the user to input a set-point, or target, body temperature for the patient 12. The display 94, for example, could display this set-point temperature along with the actual body temperature of the patient 12, the temperature of the heat transfer liquid 18, and the flow rate of the heat transfer liquid, among other things.

Figure 12:
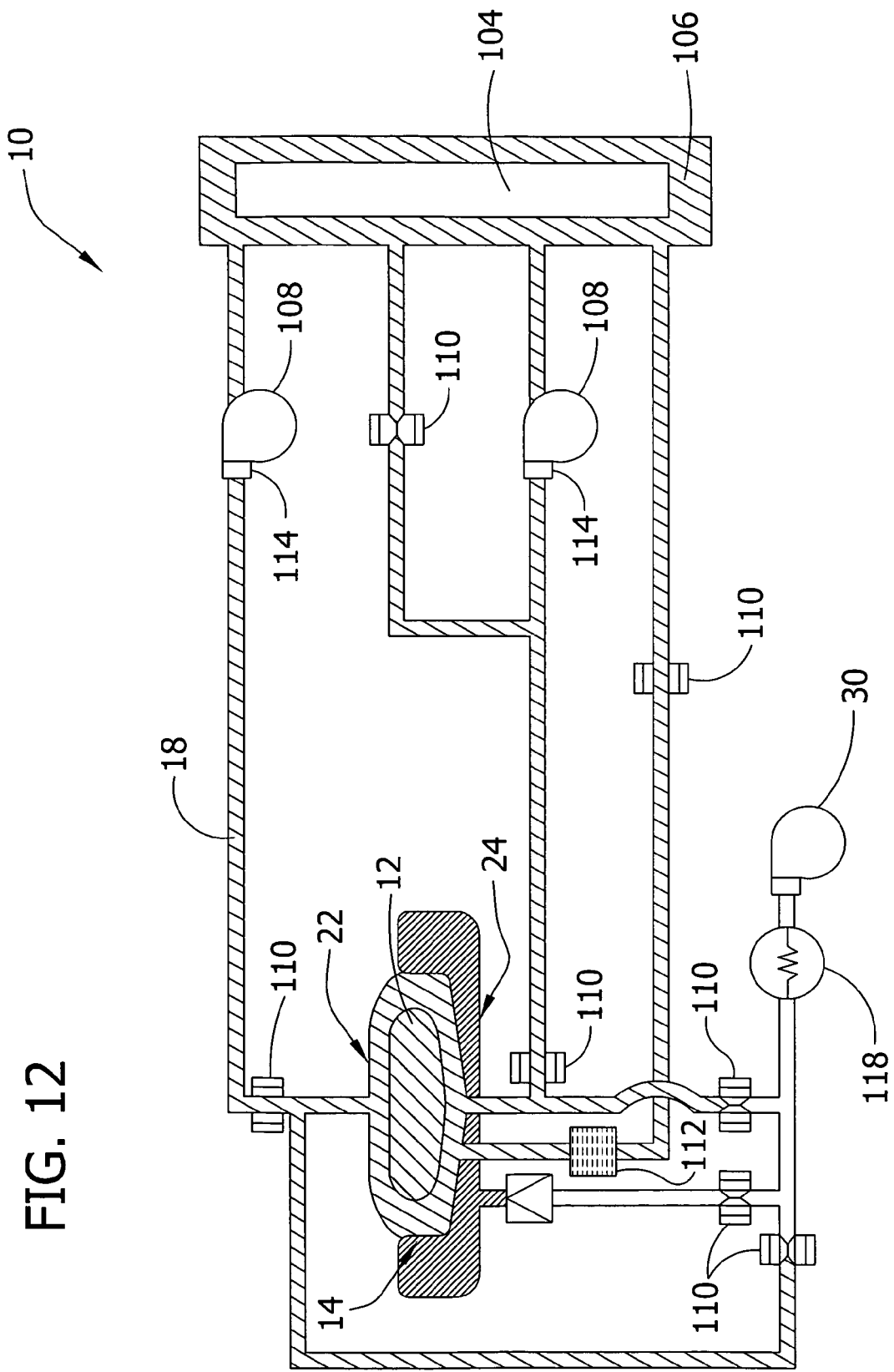
FIG. 12 is a schematic of the apparatus of the present invention showing two inlet pumps pumping heat transfer liquid into an interior space of the apparatus from the bottom and top.
Figure 13:
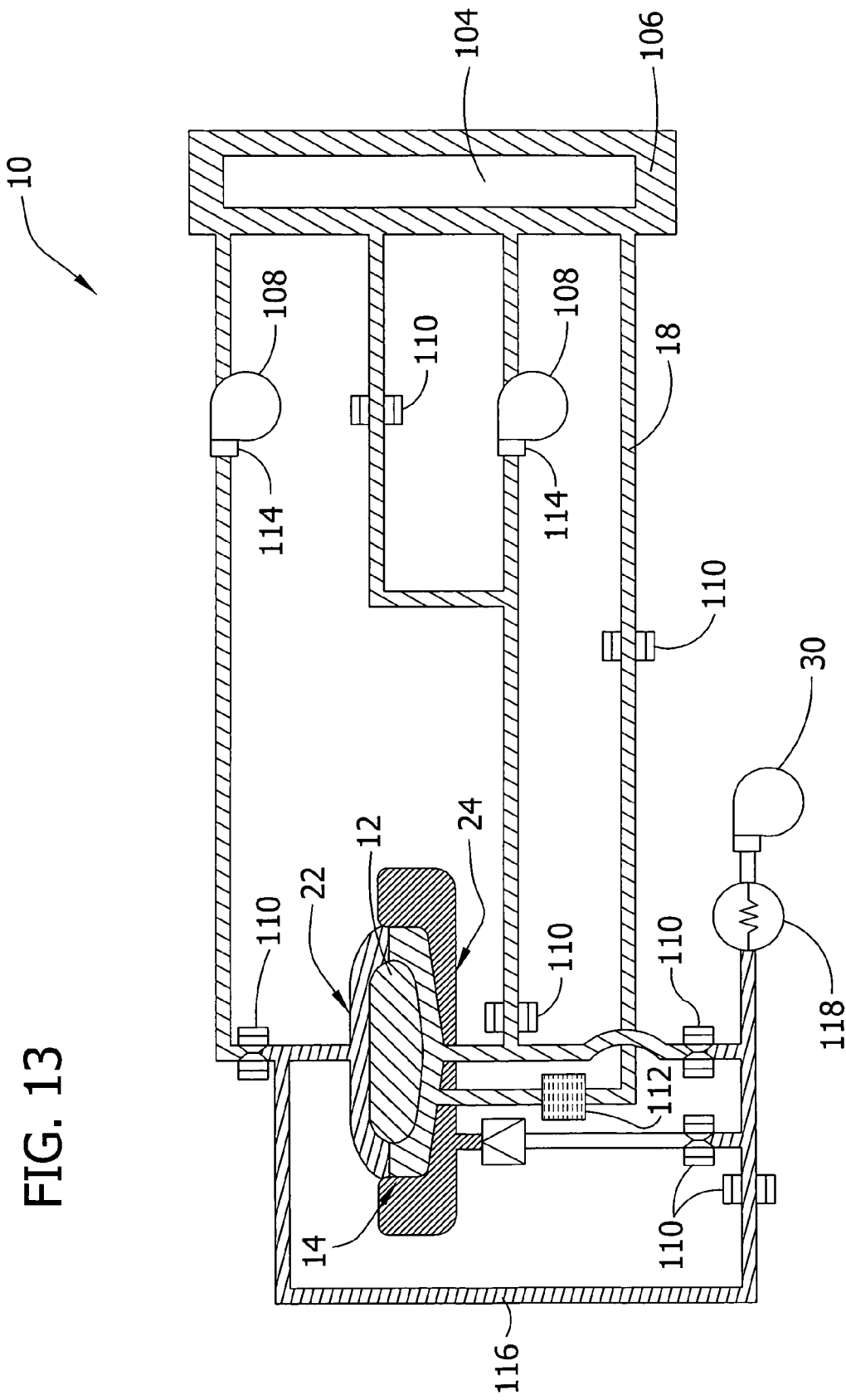
FIG. 13 is a schematic of the apparatus of the present invention showing the heat transfer liquid being exhausted from the interior space of the apparatus.
Figure 14:
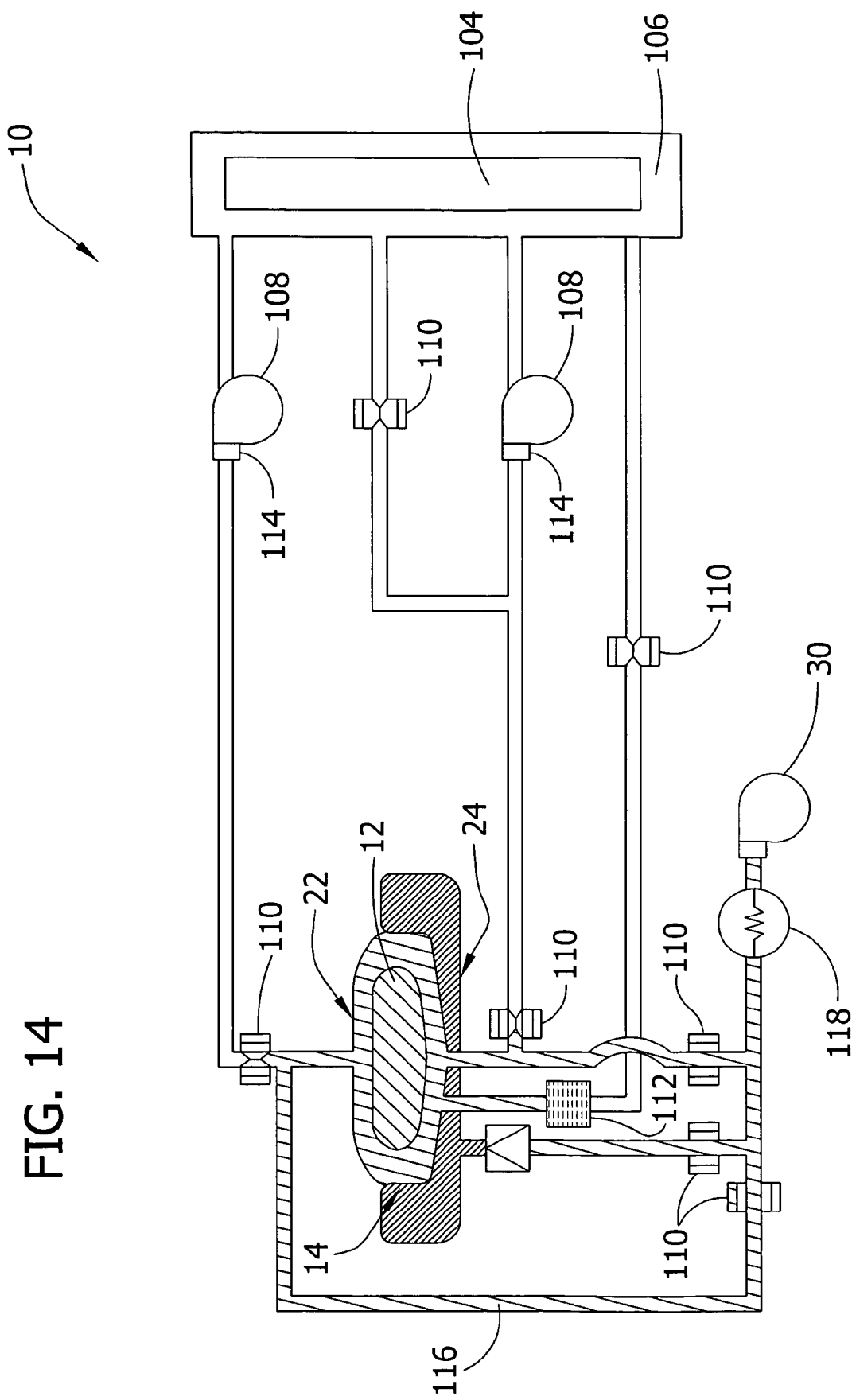
FIG. 14 is a schematic of the apparatus of the present invention showing the air pump pumping heat transfer gas into the interior space of the apparatus.

The delivery system 92 of the control system 86 comprises a liquid delivery system 100 which is a generally closed, continuous flow system in which heat transfer liquid 18 exhausted from the outlet 80 is directed to flow back to the passages 68 of the enclosure 14 for flow through the inlets 72 and into the interior space 16 of the enclosure (FIG. 12), and a gas delivery system 102 that delivers pressurized air to inflate the tubes 28 of the compliant support 24 (FIG. 11) and to flow into the enclosure 14 for direct contact with the patient's body (FIG. 14). With reference to FIGS. 12 and 13, the delivery system 92 comprises a liquid heat exchanger 104, a gas heat exchanger 118, a fluid reservoir 106, three pumps (two liquid pumps 108 and one air pump 30), a plurality of valves 110, and a filtration system 112. It is understood that the delivery system 92 can have fewer or more components without departing from the scope of this invention.

The heat exchanger 104 of the liquid delivery system 100 is used to alter the temperature of the heat transfer liquid 18 to an inlet temperature Ti, measured before the liquid enters the enclosure 14. Heat transfer liquid 18 exhausted from the enclosure 14 may be reintroduced into the enclosure as described above after passing through the heat exchanger 104. The heat exchanger 104 alters the temperature of the exhausted heat transfer liquid 18 from an outlet temperature $T_o$, measured after the liquid exits the enclosure 14, to the inlet temperature $T_i$. This allows the same heat transfer liquid 18 to be used repeatedly between the enclosure 14 and the liquid delivery system 100. Various types of heat exchangers 104 are contemplated as being within the scope of the present invention. For instance, the heat exchanger 104 of the present invention may incorporate a Peltier device and/or a phase-change material to facilitate returning the heat transfer liquid 18 to its inlet temperature $T_i$ after passing through the enclosure 14 and being altered by the temperature of the patient's body. It is understood that the heat exchanger 104 can be used to warm or cool the heat transfer liquid 18. In the illustrated embodiment, the heat exchanger 104 is approximately 10 pounds of a phase change material (e.g., ice) placed in the reservoir 106 for direct contact with the heat transfer liquid 18 within the reservoir. It is appreciated that more or less of the phase change material may be used and that the heat exchanger 104 can be placed at other locations in the liquid distribution system 100.

The reservoir 106 holds heat transfer liquid 18 at the temperature induced by the heat exchanger 104 and stores it before the inlet pumps 108 pump the liquid into the enclosure 14. The reservoir 106 may have insulation (not shown) to help maintain the temperature of the heat transfer liquid 18 before it is pumped into the enclosure 14. Although various sized reservoirs may be used, the reservoir 106 in the illustrated embodiment has a capacity of about 16 liters (4.2 gallons). It is understood that reservoirs having different capacities may be used. For example, the reservoir 106 for holding heat transfer liquid 18 for the child or baby sized enclosure 14 may have a smaller capacity where as a reservoir for holding heat transfer liquid for a larger enclosure would have a larger capacity.

As shown in FIG. 12, two of the pumps are inlet pumps 108 in fluid communication with the reservoir 106 and the passages 68 of the enclosure 14 for pumping heat transfer liquid 18 from the reservoir into the enclosure at a flow rate of about 5 liters per minute (1.3 gallons per minute). As illustrated, one of the inlet pumps 108 directs heat transfer liquid to the passage 68 in the impermeable member 26 of the cover 22 for directing heat transfer liquid 18 over the top of the patient body, and the other inlet pump directs heat transfer liquid to the passage in the impermeable member 48 of the compliant support 24 thereby directing heat transfer liquid underneath the patient's body. Each of these pumps 108 can be operated independently of the other. Accordingly, heat transfer liquid 18 can be selectively directed for flow over the top of the patient's body, underneath the patient's body, or both (i.e., over the top of the patient's body and underneath the patient's body).

The pumps 108 may be a gear pump, such as the UGP-2000 series manufactured by B&D Pumps, Inc. of Huntley, Ill., USA, or a roller-type pumphead with a motor drive, such as the 500 series process pump manufactured by Watson-Marlow OEM of Paramus, N.J., USA. Moreover, the pumps may have detachable pumpheads 114 that are disposable to minimize the likelihood of cross-contamination to subsequent patients. The pumpheads 114 are the only part of the pump 108 that contacts the heat transfer liquid 18. For example, the pumphead 114 may be made from a relatively inexpensive plastic material and easily attachable and detachable from the pump 108. For example, the pumpheads 114 made be from a plastic material and attached to the pump 108 using bolts. Thus, after use, the pumphead 114 can be removed from the pump 108, discarded properly, and a new pumphead installed on the pump for use with another patient. Should higher flow rates or other parameters be required, alternative pumps, such as higher capacity gear or centrifugal pumps, may be used without departing from the scope of the present invention.

The filtration system 112 is in fluid communication with the outlet 80 of the enclosure 14 for filtering the heat transfer fluid 18 as it is exhausted thereby preventing potential contamination with other components of the liquid delivery system 100 (i.e., the inlet pumps 108 and reservoir 106). The filtration system 112 comprises a particular matter filter, activated carbon, and an ultraviolet light to kill bacteria and viruses. One such filtration system is the Aqua Sun Model SWP-V2 manufactured by Aqua Sun International, of Minden, Nev., USA. The filtration system 112 can be located anywhere within the liquid delivery system 100 or have more or fewer filtration capabilities without departing from the scope of this invention.

The air delivery system 102 comprises an air pump 30, such as a conventional reciprocating or scroll-type compressor, in fluid communication with the compliant support 24 for inflating the tubes 28 (FIG. 11), and the enclosure 14 for directing air 116 (broadly, "heat transfer gas") into the enclosure (FIG. 14). Apart from its function of supplying a heat transfer gas 116, the air pump 30 is adapted to fill the tubes 28 of the compliant support 24 with air. For example, the pump 30 may have the capacity to fill the tubes 28 of the compliant support 24 with air at a rate of about 500 liters per minute to a positive gauge pressure of about 2 kilopascals (0.3 pounds per square inch). It is understood that other types of air pumps can be used and that the air pumps can have different flow rates then those indicated.

The air pump 30 is also used to pump air into the enclosure for heat transfer purposes (FIG. 14). The air heat exchanger 118, such as an inline air heater or cooler, can be used to alter the temperature of the air prior to it being pumped into the enclosure. Accordingly, the temperature altered air 116 can be directed into the enclosure to adjust the temperature of the patient received in the enclosure. This feature is particularly useful when heat transfer liquid 18 or phase change materials are unavailable. Moreover, temperature altered air 116 can be used to maintain the temperature of the patient 12 at a target temperature. For example, the heat transfer liquid 18 can be directed into the enclosure 14 to rapidly adjust the temperature of the patient 12 to, or near, a target temperature, and then temperature altered air 116 can be used to maintain the temperature of the patient at the selected target temperature. In addition, warm air can be used to suppress shivering sometimes experienced by patients whose temperature has been lowered.

As shown in FIGS. 11-14, the valves 110 provide control over the flow paths of both the heat transfer liquid 18 and the heat transfer gas 116 through the delivery system 92. The valves 110, such as pinch valves, are movable from a closed position in which the heat transfer liquid 18 (or heat transfer gas 116) is inhibited from flowing past the valve, to an open position where the heat transfer liquid (or heat transfer gas) is uninhibited to flow past the valve. For example, one of the valves 110 is positioned along the flow path between the passage 68 formed in the impermeable member 48 of the compliant support 24 and the reservoir 106. In the closed position, this valve 110 inhibits flow past the valve to the reservoir 106 and thereby allows the heat transfer liquid 18 to be pumped by the inlet pump 108 into the bottom of the interior space 16 of the enclosure 14. In the opened position and with the inlet pump 108 shut off, the valve 110 allows the heat transfer liquid 18 to flow via gravity through the passage 68 in the impermeable member 48 of the compliant support 24 and past the valve to the reservoir 106. The other valves 110 of the apparatus 10 control flow in other sections of the delivery system 92 in a similar manner. Other types of valves and other valves configurations are contemplated as being within the scope of this invention.

In operation, the enclosure 14 is placed on a generally flat surface, such an ambulance gurney 20. The compliant support 24 is fully extended to a position such that the underside of the compliant support is resting on the gurney. The cover 22 is disengaged from the compliant support 24, if necessary, and moved about the edge 60 toward the rear end panel 54 of the enclosure 14 thereby exposing the center of the compliant support 24. The patient 12 is carefully placed in the center of the compliant support 24 on the porous layer 50 overlying the impermeable member 48 and aligned with the positioner 56 (i.e., the face of the patient 12 is aligned with the image of a face) to ensure proper patient placement. The air pump 30 is then activated to inflate the tubes 28 to the desired pressure (FIG. 11), and thereby conform the interior surfaces 36 of the tubes 28 to the portion of the patient's body juxtaposed thereto. The air pump 30 can be activated anytime during use to maintain the tubes 28 at the desired pressure. The cover 22 is then positioned to cover the patient's body from the neck downward. The sealing portions 62, 64 of the cover 22 and the compliant support 24 are engaged thereby enclosing the patient 12 in the enclosure 14.

Using the control unit 88, the delivery system 92 is then activated to deliver either heat transfer liquid 18 or heat transfer gas 116 to the patient's body to adjust the temperature of the patient 12 to a selected temperature (FIG. 12). For example, it may be desirable to quickly lower the body temperature of a patient 12 suffering from cardiac arrest from about 37° C. (98.6° F.) to about 28° C. (82.4° F.). In this example, approximately 16 liters (4.2 gallons) of the heat transfer liquid 18 (e.g., water) and approximately 4.5 kilograms (10 pounds) of phase change material (e.g., ice) are added to the reservoir 106. It may be desirable to use pre-cooled heat transfer liquid 18. The heat transfer liquid 18, which is lowered to a temperature between about 0.5° C. (32.9° F.) and about 4° C. (39.2° F.) is then pumped through the passages 68 and inlets 72 and into the top and bottom of the enclosure 14 by the two inlet pumps 108 such that heat transfer liquid 18 is in direct contact with the patient's body at a flow rate of about 5 liters per minute (1.3 gallons per minute). The heat transfer liquid 18 below the patient's body flows through the passage created by the porous layer 50. In addition to being able to pump heat transfer liquid 18 into both the top and bottom of the enclosure 14 simultaneously, the inlet pumps 108 can be selectively operated to pump heat transfer liquid 18 only into the top of the enclosure or only into the bottom of the enclosure.

Heat transfer liquid 18 accumulates in the well 58 created by the patient 12 in the compliant support 24 such that a greater volume of heat transfer liquid accumulates in the region of the compliant support that receives the torso than the regions of the compliant support that receive the head, legs, and feet. The heat transfer liquid accumulates in the interior space 16 of the enclosure 14 until it reaches a height greater than the spillway created by the drain tube 82 in fluid communication with the outlet 80. The drain tube 82 maintains the heat transfer liquid 18 at a target depth of about 14 centimeters (5.5 inches), which creates a positive gauge pressure at the outlet 80 of the enclosure 14 of about 1.4 kilopascals (0.2 psi). Any heat transfer liquid 18 achieving a height greater than the spillway created by the drain tube 82 will be exhausted from the enclosure at a flow rate equal to or greater than flow rates at which the heat transfer liquid is being driven into the interior space 16 of the enclosure 14 by the inlet pumps 108.

The heat transfer liquid 18 exhausted from the enclosure 14 passes through the filtration system 112 to remove contamination from the patient 12, such as particulate matter, viruses, and bacteria. The filtered heat transfer fluid 18 is directed back into the reservoir 106 where it is re-cooled by the phase change material prior to be recirculated into the interior space 16 of the enclosure 14. Heat transfer fluid 18 is continuously recirculated through the enclosure 14 until the patient's temperature reaches or approaches the selected temperature. The patient's temperature may drop slightly even after the heat transfer liquid 18 has been stopped and, as a result, it may be desirable to stop the flow of heat transfer liquid short of the selected temperature to prevent overshoot (i.e., lowering the patient's body temperature below the selected temperature). At this point, the inlet pumps 108 are shut off and the heat transfer liquid 18 is exhausted from the enclosure 14 via gravity. Once the inlet pumps 108 are shut off, the valves 110 are adjusted to allow heat transfer liquid 18 to be exhausted from the interior space 16 of the enclosure 14 though the inlets 72 in communication with the passages 68 in the compliant support 24 (FIG. 13). The air pump 30 can be used to pump air into the top of the enclosure 14 to more rapidly exhaust the heat transfer liquid 18 from the enclosure. Further yet, the inlet pump 108 in fluid communication with the bottom of the enclosure 14 can be used as an outlet pump to pump heat transfer liquid 18 from the interior space 16 of the enclosure back to the reservoir 106.

The patient 12 can be maintained at the selected temperature by turning on the air pump 30 and directing the air pumped by the air pump through the inline heat exchange 118 (FIG. 14). The cooled heat transfer gas 116 is directed to flow into the passages 68 and through the inlets 72 of the enclosure 14 for direct contact with the patient's body. It is believed that the patient's body temperature can be maintained using heat transfer gas 116 for a desired period of time up to about 12 to 24 hours. The heat transfer gas 116 exits the interior space 16 of the enclosure 14 through the unsealed portion of the enclosure adjacent the patient's neck and/or the outlet 80.

The heat transfer gas 116 can also be used to induce slower temperature changes in the patient 12 than the heat transfer liquid 18 or to suppress shivering. In addition, heat transfer gas 116 can be used at remote locations away from the ambulance or a reservoir 106 of heat transfer liquid 18. This relieves the user of the need to transport heavy heat transfer liquid 18 and phase change materials to the patient without delaying treatment of the patient. After the patient has been transported to a suitable location (e.g., ambulance, hospital), heat transfer liquid 18 can be introduced into the interior space 16 of the enclosure 14.

It is understood that during the above mention operations, the user is able to maintain visual observation of the patient's body through the transparent cover 22. If additional medical care is needed, the cover 22 can be pulled back about edge 60(or completely removed), with the delivery system operating 92, to expose the patient's body. The delivery system 92 will continue to direct the heat transfer liquid 18 or heat transfer gas 116 to the underside of the patient's body. If the liquid delivery system 100 is being used, the inlet pump 108 directing heat transfer liquid 18 to the passage 68 in the cover 22 can be shut off before the cover is pulled back to prevent any heat transfer liquid 18 from spilling from the apparatus 10. Moreover, all of the apparatus' operations can occur in the ambulance on route to the medical facility thereby not delaying any subsequent medical care.

Figure 15:
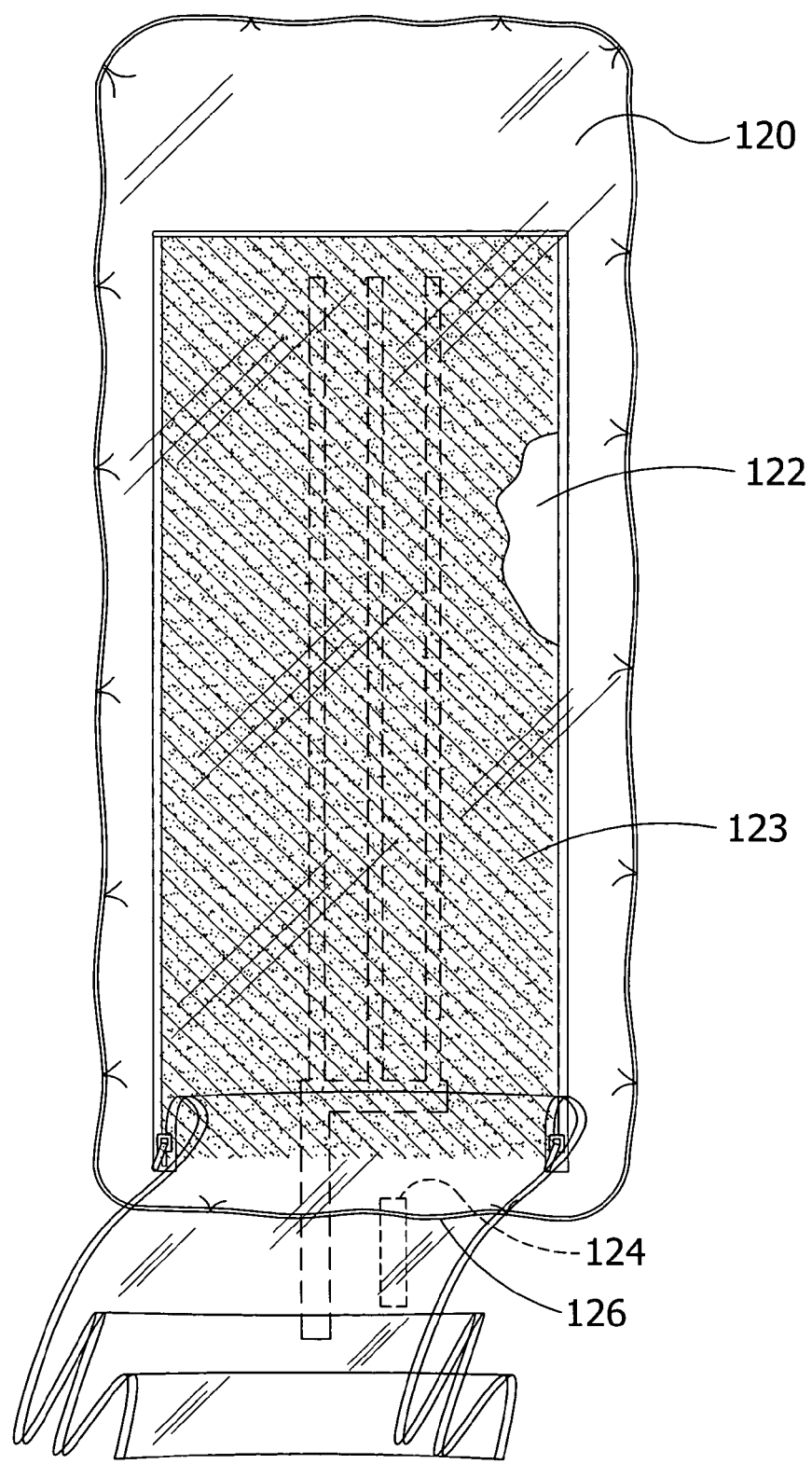
FIG. 15 is a top plan of the apparatus with the cover pulled back to show another configuration of the compliant support.
Figure 16:
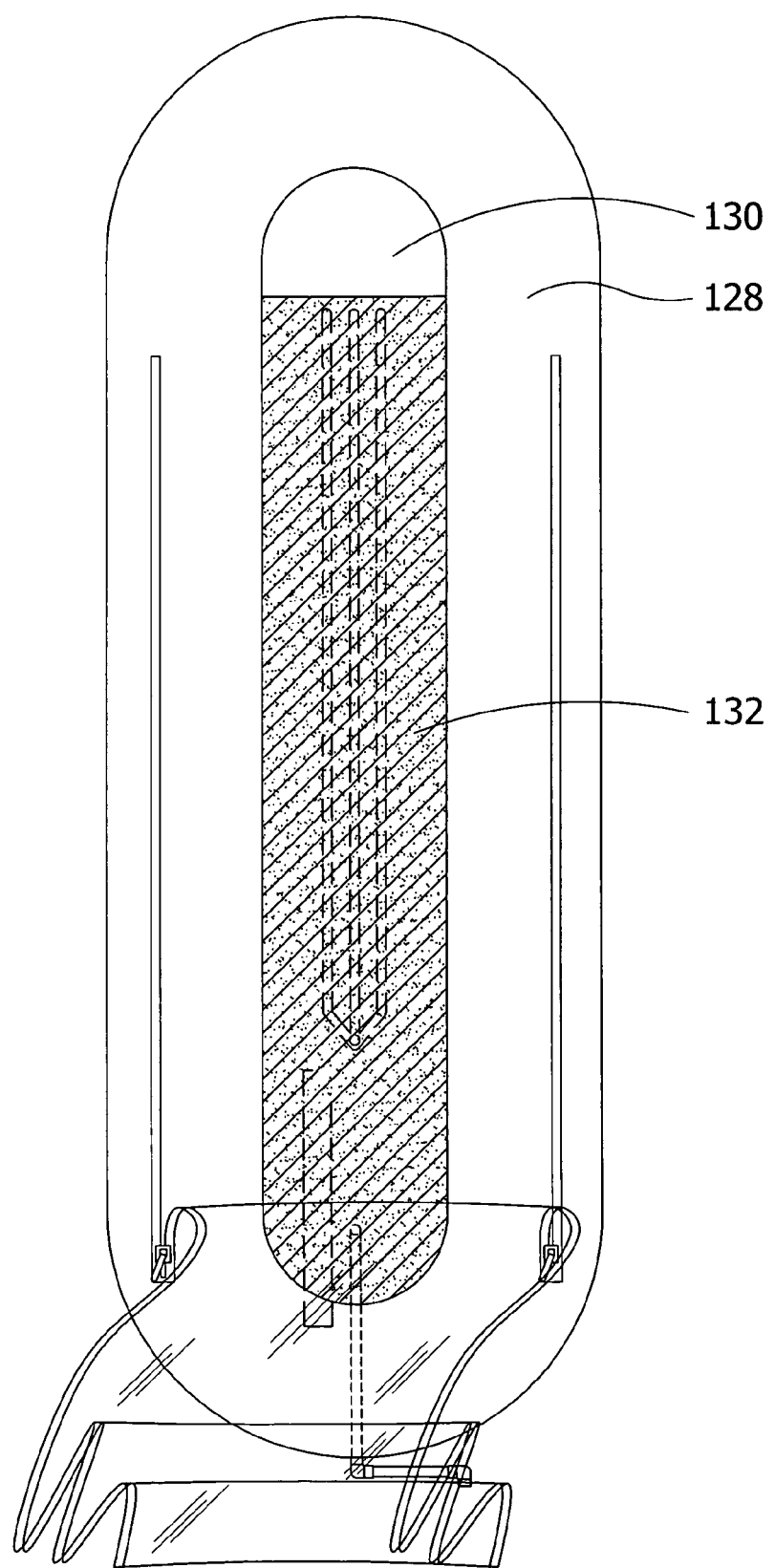
FIG. 16 is a top plan of the apparatus with the cover pulled back to show yet another configuration of the compliant support.

FIGS. 15 and 16 illustrate other configurations of the compliant support 24. The compliant support 24 illustrated in FIG. 15 comprises a generally rectangular air mattress 120. The air mattress 120 is only partially inflated thereby allowing a well to form under the weight of the patient (not shown) placed on the mattress. A rectangular impermeable member 122 of substantially the same construction as described above overlies and is affixed to the mattress 120. A batting layer 123 is placed over the impermeable member 122. A portion of the batting layer 123 is cut away in FIG. 15 to show the underlying impermeable member 122. An outlet 124 is fluid communication with the well 121 and a conduit extending through a rear end panel 126 of the mattress 120 for exhausting heat transfer liquid from the interior space of the enclosure.

In the configuration of FIG. 16, the compliant support 24 comprises an inflatable, oblong tube 128 extending around the entire periphery of the support. An impermeable member 130 of substantially the same construction as described above is located in the center of the oblong tube 128 and is bonded to an underside of the oblong tube about its entire circumference to define a water tight well 132 for receiving the patient's body.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. Apparatus for altering the body temperature of a patient, the apparatus comprising:
    a cover for covering at least a portion of a patient's body;
    a compliant support adapted to underlie and generally conform to the shape of the portion of the patient's body to define a well adjacent to the patient's body portion for accumulating heat transfer liquid, said compliant support comprising a gas-filled mattress;
    the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

2. Apparatus as set forth in claim 1 wherein said compliant support is generally rectangular.

3. Apparatus as set forth in claim 1 wherein said compliant support is generally oblong.

4. Apparatus as set forth in claim 1 further comprising at least one passage for directing the heat transfer liquid into the enclosure.

5. Apparatus as set forth in claim 4 wherein the passage is located below the portion of the patient's body received in the enclosure.

6. Apparatus as set forth in claim 5 wherein at least a portion of the passage includes a hold-open to hold the passage open and permit flow of a heat transfer liquid through the passage past the hold-open.

7. Apparatus as set forth in claim 6 further comprising a sheet-like body-facing component and a sheet-like outer component, said sheet-like body-facing component and sheet-like outer component being joined in face-to-face arrangement with one another, said components further being joined to one another along their facing sides to form the passage between the components.

8. Apparatus as set forth in claim 1 wherein said compliant support is sized and shaped for being placed on a stretcher.

9. Apparatus as set forth in claim 8 wherein said compliant support has a width between about 66 centimeters (26 inches) and about 76 centimeters (30 inches) and a length between about 203 centimeters (80 inches) and about 210 centimeters (83 inches).

10. Apparatus as set forth in claim 1 in combination with a stretcher.

11. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid, said compliant support having a right side, a left side, and a center, said compliant support comprising at least one gas-filled tube extending along the right and left sides and generally defining a recess in the center;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

12. Apparatus as set forth in claim 11 wherein said compliant support further comprises a component extending between the gas-filled tube on the right and left side of the support.

13. Apparatus as set forth in claim 12 wherein the gas-filled tube has a foot end and a head end, said component being attached to the tube such that said component slopes from the head end toward the foot end.

14. Apparatus as set forth in claim 11 wherein said compliant support further comprises a front and a rear, said gas-filled tube extending along the front and rear.

15. Apparatus as set forth in claim 11 wherein said compliant support further comprises a front end panel and a rear end panel.

16. Apparatus as set forth in claim 15 wherein said end panels are bonded to the gas-filled tubes extending along the right and left sides of the compliant support.

17. Apparatus as set forth in claim 15 further comprising a head rest for supporting at least a portion of the patient's head.

18. Apparatus as set forth in claim 15 wherein said at least a portion of each end panel is inflatable.

19. Apparatus as set forth in claim 11 wherein the recess has a depth between about 2.5 centimeters (2.8 inches) and 20 centimeters (8 inches).

20. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid;
 a porous layer disposed between said compliant support and the portion of the patient's body received in the enclosure.

21. Apparatus as set forth in claim 20 wherein the porous layer is batting.

22. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid, said compliant support comprising a tapered pocket for receiving the feet of the patient;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

23. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid, said compliant support comprising a pocket sized and shaped for receiving the head of the patient;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

24. Apparatus as set forth in claim 23 further comprising a rest for supporting at least a portion of the patient's head.

25. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid;
 a restraint engageable with exterior-facing sides of the compliant support, said exterior-facing sides being captured by the restraint to limit outward expansion of the compliant support.

26. Apparatus as set forth in claim 25 wherein said restraint is a rigid material.

27. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid, said compliant support comprising a front end panel;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

28. Apparatus for altering the body temperature of a patient, the apparatus comprising:
 a cover for covering at least a portion of a patient's body;
 a compliant support adapted to underlie and generally conform to the shape of the portion of the patient's body to define a well adjacent to the patient's body portion for accumulating heat transfer liquid, said compliant support comprising a rear end panel;
 the cover and compliant support cooperatively defining an enclosure for receiving the portion of the patient's body and being constructed to conduct a heat transfer liquid into direct contact with the portion of the patient's body received in the enclosure to promote heat transfer between the patient's body and the heat transfer liquid.

29. Apparatus for altering the body temperature of a patient, said apparatus comprising:
 an enclosure adapted for receiving at least the torso and the legs of a patient, said enclosure being capable of conforming to the shape and size of the patient's body to thereby accommodate patients of various shapes and sizes, said enclosure comprising a well for holding a volume of heat transfer fluid, said well being adapted to adjust said volume of heat transfer fluid to the particular shape and size of the patient's body received in said enclosure;
 a liquid delivery system capable of driving heat transfer liquid into the enclosure for direct contact with at least a portion of the patient's torso received in the enclosure to promote heat transfer between the patient's body and the heat transfer liquid.

30. Apparatus as set forth in claim 29 wherein said well is capable of holding a greater volume of heat transfer fluid for a larger patient than for a smaller patient.

31. Apparatus as set forth in claim 29 wherein said enclosure is adapted to receive patients selected from a group of patients including babies, children, and adults.

32. Apparatus as set forth in claim 31 wherein said enclosure is adapted to receive adult patients between about the $5^{th}$ percentile and about the $95^{th}$ percentile adult male.

33. Apparatus as set forth in claim 29 wherein said enclosure comprises a cover for covering at least a portion of a patient's body, and a compliant support adapted to underlie the patient's body portion.

34. Apparatus for altering the body temperature of a patient, the apparatus comprising:
 a compliant support sized and shaped for receiving a portion of the patient's body and constructed to conduct a heat transfer liquid into direct contact with the portion of the patient's body received in the enclosure to promote heat transfer between the patient's body and the heat transfer liquid, said compliant support being adapted to underlie and generally conform to the shape of the portion of the patient's body to define a well adjacent to the patient's body portion for accumulating heat transfer liquid, said compliant support having a right side, a left side, and a center, said compliant support comprising at least one gas-filled tube extending along the right and left sides and generally defining a recess in the center; and
 a liquid delivery system for driving the heat transfer liquid into the enclosure.

35. Apparatus as set forth in claim 34 wherein said liquid delivery system comprises a pump for pumping the heat transfer liquid into the enclosure.

36. Apparatus as set forth in claim 34 in combination with a cover for covering at least a part of the portion of a patient's body.

37. Apparatus as set forth in claim 34 wherein said compliant support further comprises a component extending between the gas-filled tube on the right and left side of the support.

38. Apparatus as set forth in claim 37 wherein the gas-filled tube has a foot end and a head end, said component being attached to the tube such that said component slopes from the head end toward the foot end.

39. Apparatus as set forth in claim 38 wherein said compliant support is sized and shaped for being placed on a stretcher.

40. Apparatus as set forth in claim 39 wherein said compliant support has a width between about 66 centimeters (26 inches) and about 76 centimeters (30 inches) and a length between about 203 centimeters (80 inches) and about 210 centimeters (83 inches).

41. Apparatus for altering the body temperature of a patient, the apparatus comprising:
 a compliant support sized and shaped for underlying at least a portion of the patient's body and adapted to minimize pressure concentrations beneath the patient to inhibit sores developing on the patient, the compliant support being adapted to allow a heat transfer liquid to flow adjacent the patient's body for promoting heat transfer between the portion of the patient's body and the heat transfer liquid, and
 a porous layer comprising a batting being disposed between the compliant support and the portion of the patient's body.

42. Apparatus for altering the body temperature of a patient, the apparatus comprising a compliant support sized and shaped for underlying at least a portion of the patient's body and adapted to minimize pressure concentrations beneath the patient to inhibit sores developing on the patient, the compliant support being adapted to allow a heat transfer liquid to flow adjacent the patient's body for promoting heat transfer between the portion of the patient's body and the heat transfer liquid, the compliant support being a gas-filled mattress adapted to generally conform to the shape of the patient's body when the patient's body rests on the support.

* * * * *